United States Patent
Herrmann et al.

(10) Patent No.: US 11,813,266 B2
(45) Date of Patent: *Nov. 14, 2023

(54) COMBINATION OF ACTIVE AGENTS FOR THE TREATMENT OF PROGRESSIVE FIBROSING INTERSTITIAL LUNG DISEASES (PF-ILD)

(71) Applicant: Boehringer Ingelheim International GmbH, Ingelheim am Rhein (DE)

(72) Inventors: Franziska Elena Herrmann, Weilheim (DE); Peter Nickolaus, Warthausen (DE); Stefan Ludwig Michael Wollin, Bad Waldsee (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 16 days.

This patent is subject to a terminal disclaimer.

(21) Appl. No.: 17/811,914

(22) Filed: Jul. 12, 2022

(65) Prior Publication Data

US 2022/0378793 A1 Dec. 1, 2022

Related U.S. Application Data

(63) Continuation of application No. 16/166,239, filed on Oct. 22, 2018, now Pat. No. 11,406,638.

(30) Foreign Application Priority Data

Oct. 23, 2017 (EP) ..................... 17197719

(51) Int. Cl.
*A61K 31/519* (2006.01)
*A61P 11/00* (2006.01)
(Continued)

(52) U.S. Cl.
CPC .......... *A61K 31/519* (2013.01); *A61K 31/496* (2013.01); *A61K 31/505* (2013.01); *A61P 11/00* (2018.01)

(58) Field of Classification Search
CPC .. A61K 31/496; A61K 31/505; A61K 31/519; A61P 11/00
See application file for complete search history.

(56) References Cited

U.S. PATENT DOCUMENTS

| | | |
|---|---|---|
| 3,974,281 A | 8/1976 | Gadekar |
| 5,712,298 A | 1/1998 | Amschler |
(Continued)

FOREIGN PATENT DOCUMENTS

| | | |
|---|---|---|
| WO | 0127081 A1 | 4/2001 |
| WO | 2004013099 A1 | 2/2004 |
(Continued)

OTHER PUBLICATIONS

"Increased fibroblast telomerase expression precedes myofibroblast a-smooth muscle actin expression in idiopathic pulmonary fibrosis", Clinics (Sao Paulo), 2012;67:1039-1046.
(Continued)

*Primary Examiner* — Rayna Rodriguez
(74) *Attorney, Agent, or Firm* — Philip I. Datlow

(57) ABSTRACT

The application refers to a novel combination treatment/combination medicament for PF-ILD treatment, comprising as a first combination partner a therapeutically effective amount of Nintedanib or a pharmaceutically acceptable salt thereof and as a second combination partner a therapeutically effective amount of a PDE4B-inhibitor of formula I (Continued)

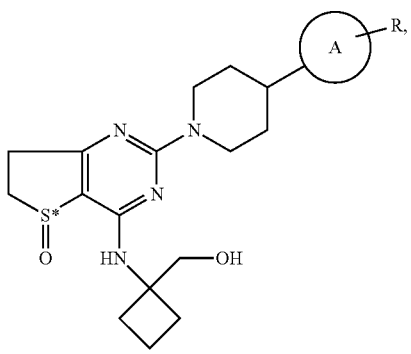

Figure 1:
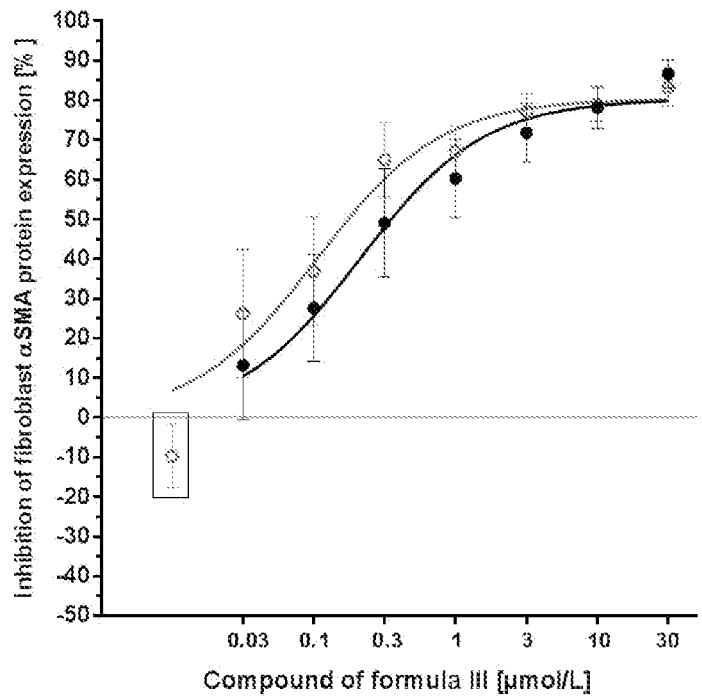

wherein Ring A is a 6-membered aromatic ring which may optionally comprise one or two nitrogen atoms and
wherein R is Cl and wherein R may be located either in the para-, meta- or ortho-position of Ring A,
wherein S* is a sulphur atom that represents a chiral center or a pharmaceutically acceptable salt thereof.
Hereby the second combination partner is preferably a therapeutically effective amount of the PDE4B-inhibitior of formula III

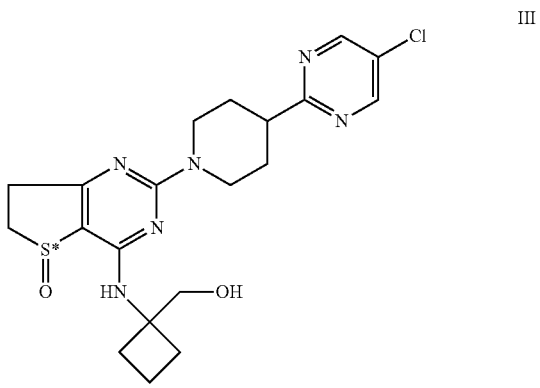

or a pharmaceutically acceptable salt thereof.

7 Claims, 3 Drawing Sheets

(51) Int. Cl.
  *A61K 31/496*  (2006.01)
  *A61K 31/505*  (2006.01)

(56)  References Cited

U.S. PATENT DOCUMENTS

| | | | |
|---|---|---|---|
| 6,020,358 | A | 2/2000 | Muller et al. |
| 6,762,180 | B1 | 7/2004 | Roth et al. |
| 7,119,093 | B2 | 10/2006 | Roth et al. |
| 7,550,472 | B2 | 6/2009 | Dollinger et al. |
| 7,723,341 | B2 | 5/2010 | Hoenke et al. |
| 8,114,878 | B2 | 2/2012 | Pouzet et al. |
| 8,609,670 | B2 | 12/2013 | Pouzet et al. |
| 9,907,756 | B2 | 3/2018 | Messerschmid et al. |
| 2006/0116373 | A1 | 6/2006 | Dollinger et al. |
| 2009/0318471 | A1 | 12/2009 | Sieger et al. |
| 2010/0305102 | A1 | 12/2010 | Pouzet et al. |
| 2011/0190318 | A1 | 8/2011 | Messerschmid et al. |
| 2014/0228286 | A1 | 8/2014 | Luippold et al. |
| 2015/0045376 | A1 | 2/2015 | Pouzet et al. |

FOREIGN PATENT DOCUMENTS

| | | |
|---|---|---|
| WO | 2006056607 A1 | 6/2006 |
| WO | 2006058867 A2 | 6/2006 |
| WO | 2006058868 A2 | 6/2006 |
| WO | 2006058869 A2 | 6/2006 |
| WO | 2006067165 A2 | 6/2006 |
| WO | 2006111549 A1 | 10/2006 |
| WO | 2007118793 A1 | 10/2007 |
| WO | 2007141283 A2 | 12/2007 |
| WO | 2009050242 A2 | 4/2009 |
| WO | 2009050248 A1 | 4/2009 |
| WO | 2009147212 A1 | 12/2009 |
| WO | 2009147220 A1 | 12/2009 |
| WO | 2013026797 A1 | 2/2013 |
| WO | 2014124860 A1 | 8/2014 |
| WO | 2017016530 A1 | 2/2017 |

OTHER PUBLICATIONS

Chang et al., "SPARC Suppresses Apoptosis of Idiophathic Pulmonary Fibrosis Fibroblasts through Constitutive Activation of β-Catenin" J Biol Chem. 2010; 285; No. 11, p. 8196-8206.
Cottin et al., "Presentation, diagnosis and clinical course of the spectrum of progressive-fibrosing interstitial lung diseases", Eur Respir Rev 2018, 27 180076, p. 1-11 Progressive-Fibrosing ILD https://doi.org/10.1183/16000617.0076-2018.
Cutroneo et al., "Therapies for Bleomycin Induced Lung Fibrosis Through Regulation of TGF-β1 Induced Collagen Gene Expression", J. Cell. Physiol. 211: 585-589, 2007.
Du Bois et al., "Strategies for treating idiopathic pulmonary fibrosis", Nat. Rev. Drug Discov. 2010, 9, 129-140.
Harari et al., "IPF: new insight on pathogenesis and treatment", Allergy, 2010, 65 (5): 537-553.
Hilberg et al., "BIBF 1120: Triple Angiokinase Inhibitor with Sustained Receptor Blockade and Good Antitumor Efficacy", Cancer Res., 2008, 68, 4774-4782.
Hostettler et al., "Anti-fibrotic effects of nintedanib in lung fibroblasts derived from patients with idiopathic pulmonary fibrosis", Respiratory Research, Biomed Central Ltd., Dec. 12, 2014, vol. 15, No. 1, pp. 1157.
Huang et al., "Nintedanib inhibits fibroblast activation and ameliorates fibrosis in preclinical models of systemic sclerosis", Ann. Rheum. Dis. 2016, 75, 883-890.
Huang et al., "Nintedanib inhibits macrophage activation and ameliorates vascular and fibrotic manifestations in the Fra2 mouse model of systemic sclerosis", Ann Rheum Dis, Aug. 16, 2017, pp. 1941-1948.
International Preliminary Report on Patentability for PCT/EP2018/077952, dated Feb. 2, 2020.
International Search Report and Written Opinion for corresponding application PCT/EP2018/0//952, dated Jan. 17, 2019.
Kaarteenaho et al., "The current position of surgical lung biopsy in the diagnosis of idiopathic pulmonary fibrosis", Respir Res , 2013; 14(1):43.
Khali et al., "Clinical Applications of TGF-βThe role of TGF-β in pulmonary fibrosis" Ciba Found Symp. 1991; 157: 194-207.
King et al., "Idiopathic pulmonary fibrosis", Lancet, 2011; 378: 1949-1961.
Klingberg et al, "The myofibroblast matrix: implications for tissue repair and fibrosis", J Pathol. 2013; 229: 298-309.
Kuhn et al., "The Roles of the Myofibroblast in Idiopathic Pulmonary Fibrosis", Am J Pathol., 1991; 138:No. 5, p. 1257-1265.
Lee at al., "Effect of nintedanib on airway inflammation and remodeling in a murine chronic asthma model", Exp Lung Res., 2017, pp. 43187-43196.
Lee et al., "Clinical impact of depression and anxiety in patients with idiopathic pulmonary fibrosis", Plos One, 2017, pp. 1-11.

(56) References Cited

OTHER PUBLICATIONS

Lehtonen et al., "Pirfenidone and nintedanib modulate properties of fibroblasts and myofibroblasts in idiopathic pulmonary fibrosis", Respiratory Research, 2016, 17: 14.
Lotvall et al., "Advances in Combination Therapy for Asthma and COPD", Wiley-Blackwell, 2011.
Maher et al., Diminished Prostaglandin E2 Contributes to the Apoptosis Paradox in Idiopathic Pulmonary Fibrosis Am J Respir Crit Care Med. 2010; 182: 73-82.
Mazzei et al, "Nintedanib in the treatment of idiopathic pulmonary fibrosis", Ther. Adv. Respir. Dis. 2015, vol. 9 [3], pp. 121-129.
Moore et al., "Regulation and Relevance of Myofibroblast Responses in Idiopathic Pulmonary Fibrosis", Curr Pathobiol Rep. Sep. 2013; 1 (3): 199-208.
Npo et al., "FoxO3a (Forkhead Box O3a) Deficiency Protects Idiopathic Pulmonary Fibrosis (IPF) Fibroblasts from Type 1 Polymerized Collagen Matrix-Induced Apoptosis via Caveolin-1 (cav-1) and Fas", Plos One, 2013, vol. 8 Issue 4, pp. 1-16.
Parikh et al., Current Medicinal Chemistry, 2016, 23:129-141.
Patel et al., "Autophagy in Idiopathic Pulmonary Fibrosis", PLoS One, 2012, (7), pp. 1-9.
Patel et al., "Pentamers Not Found in the Universal Proteome Can Enhance Antigen Specific Immune Responses and Adjuvant Vaccines" Plos One, Aug. 2012, pp. 1-13.
Poch et al., "Quantitative Estimation of Overadditive and Underadditive Drug Effects by Means of Theoretical, Additive Dose-Response Curves", Journal of Pharmacological Methods 4, 1980, pp. 179-188.
Raghu et al, "Idiopathic Pulmonary Fibrosis: Evidence-based Guidelines for; Diagnosis and Management", Am. J. Respir. Crit. Care Med, 2011, 183: 788-824.
Redente et al., "Nintedanib Reduces Pulmonary Fibrosis In A Model Of Rheumatoid Arthritis Associated; Interstitial Lung Disease", Am J Respir Crit Care Med, 2016, 193, A4170.
Tandon et al., "Nintedanib Attenuates The Polarization Of Profibrotic Macrophages Through The Inhibition Of Tyrosine Phosphorylation On Csf1; Receptor", Am J. Respir Crit Care Med, 2017;195: A2397.
Tzouvelekis et al., "Update on therapeutic management of idiopathic pulmonary fibrosis", Therapeutics and Clinical Risk Management, 2015, 11, 359-370.
Vancheri et al., "Nintedanib with Add-on Pirfenidone in Idiopathic Pulmonary Fibrosis Results of the INJOURNEY Trial", American Journal of Respiratory and Critical Care Medicine, 2018, vol. 197 No. 3, pp. 356-363.
Vartiainen et al., "Development of Inhalable Drug Formulations for Idiopathic Pulmonary Fibrosis", Drug Delivery to the Lungs 27, 2016, pp. 1-4.
Vartiainen et al., Poster presentation at the International Colloquium of Lung and Airway Fibrosis in Dublin, Sep. 2016.
White et al., "Pathogenetic mechanisms in usual interstitial neumonia/ idiopathic pulmonary fibrosis", J Pathol. 2003; 201: 343-354.
Wollin et al., "Antifibrotic and Anti- inflammatory Activity of the Tyrosine Kinase Inhibitor Nintedanib in Experimental Models of Lung Fibrosiss", J. Pharmacol. Exp. Ther., 2014, 349, 209-220.
Wollin et al., "Mode of action of nintedanib in the treatment of idiopathic pulmonary fibrosis", Eur. Respir J, 2015, 45, 1434-1445.

COMBINATION OF ACTIVE AGENTS FOR THE TREATMENT OF PROGRESSIVE FIBROSING INTERSTITIAL LUNG DISEASES (PF-ILD)

1. BACKGROUND OF THE INVENTION

Interstitial lung diseases (ILD) include a large and diverse group of more than 200 lung diseases and respiratory conditions characterized by inflammation and fibrosis of the interstitium, the tissue and space between the air sacs of the lung (see, for instance, du Bois, Nat. Rev. Drug Discov. 2010, 9, 129-140). ILDs concern alveolar epithelium, pulmonary capillary endothelium, basement membrane, perivascular and perilymphatic tissues. An ILD may occur when an injury to the lungs triggers an abnormal healing response. Ordinarily, the body generates just the right amount of tissue to repair damage. But in ILDs, the repair process goes awry and the tissue around the air sacs (alveoli) becomes scarred and thickened. This makes it more difficult for oxygen to pass into the blood stream.

Prolonged ILD may result in pulmonary fibrosis, but this is not always the case.

Therefore ILD also include the so-called Progressive Fibrosing Interstitial Lung Diseases (PF-ILDs).

In Progressive Fibrosing Interstitial Lung Diseases (PF-ILD) the response to lung injury in fibrosing ILDs includes the development of fibrosis which becomes progressive, self-sustaining and independent of the original clinical association or trigger. It is postulated that, at this stage, targeted anti-fibrotic therapy is required to slow the progression of the disease.

Based on the similarity in both, their biologic and clinical behaviors i.e. self-sustaining fibrosis and progressive decline in lung function and early mortality, it is considered justified to group patients with PF-ILD together regardless of the original ILD diagnosis.

The number of patients with the different fibrosing ILDs e.g. idiopathic non-specific interstitial pneumonia (iNSIP) or chronic hypersensitivity pneumonitis (CHP), is similar to or lower than the number of patients with IPF; the number of patients with progressive phenotype within each group, while still significant, is even lower. Therefore grouping patients with PF-ILD together is considered the only feasible way to provide efficacious therapies for all patients with progressive fibrosing interstitial lung disease.

A patient suffers from PF-ILD in case that a physician diagnosed for this patient an Interstitial Lung Disease (ILD) and that additionally at least one of the following criteria for Progressive Fibrosing Interstitial Lung Disease are fulfilled within 24 months after the first visit at physician's despite treatment with unapproved medications used in clinical practice to treat ILD as assessed by the physician (Unapproved medications used in the clinical practice to treat ILD include but are not limited to corticosteroids, azathioprine, mycophenolate mofetil (MMF), n-acetylcysteine (NAC), rituximab, cyclophosphamide, cyclosporine, tacrolimus):

- Clinically significant decline in Forced Vital Capacity (FVC) % predicted based on a relative decline of ≥10%
- Marginal decline in FVC % predicted based on a relative decline of ≥5 to ≥10% combined with worsening of respiratory symptoms
- Marginal decline in FVC % predicted based on a relative decline of ≥5 to ≥10% combined with increasing extent of fibrotic changes on chest imaging
- Worsening of respiratory symptoms as well as increasing extent of fibrotic changes on chest imaging. Hereby changes attributable to comorbidities e.g. infection, heart failure must be excluded.
- Fibrosing lung disease on High-Resolution Computed Tomography (HRCT), defined as reticular abnormality with traction bronchiectasis with or without honeycombing, with disease extent of ≥10%, performed within 12 months after first visit at physician's.
- For patients with underlying Connective Tissue Disease (CTD): stable CTD as defined by no initiation of new therapy or withdrawal of therapy for CTD within 6 weeks prior to first visit at physician's.
- Carbon Monoxide Diffusion Capacity (DLCO) corrected for Haemoglobin (Hb) at first visit at physician's ≥30% and <80% predicted of normal at second visit at physician's.
- FVC≥45% predicted at second visit at physician's.

Examples of PF-ILDs are Idiopathic pulmonary fibrosis (IPF), Idiopathic Non-Specific Interstitial Pneumonia (iNSIP), Hypersensitivity Pneumonitis (HP), Unclassifiable Idiopathic Interstitial Pneumonias, Rheumatoid Arthritis ILD (RA-ILD), Sjögren's syndrome ILD, Systemic Lupus Erythematous ILD (SLE-ILD), Polymyositis and Dermatomyositis ILD (PM/DM-ILD), Mixed Connective Tissue Disease ILD (MCTD-ILD), Systemic Sclerosis ILD (SSc-ILD), other Connective Tissue Disease ILDs (CTD-ILD), Sarcoidosis, Asbestosis, Silicosis.

The most prominent PF-ILDs are Idiopathic Pulmonary Fibrosis (IPF) and Systemic Sclerosis Interstitial Lung Disease (SSc-ILD). Idiopathic Pulmonary Fibrosis (IPF) is a PF-ILD for which no obvious cause can be identified (which is the definition for "idiopathic") and which is associated with typical findings both radiographic (basal and pleural based fibrosis with honeycombing) and pathological (temporally and spatially heterogeneous fibrosis, histopathologic honeycombing and fibroblastic foci).

Idiopathic pulmonary fibrosis (IPF) is a chronic fibrotic irreversible and ultimately fatal lung disease characterized by a progressive fibrosis in the interstitium in the lung, leading to a decreasing lung volume and progressive pulmonary insufficiency. IPF is also characterized by a specific histopathologic pattern known as usual interstitial pneumonia (UIP) (Raghu et al, Am. J. Respir. Crit. Care Med. 183: 788-824.). The lung functions in patients with lung fibrosis either caused by IPF or any other PF-ILD is determined as forced vital capacity (FVC).

The term IPF means scarring of lung tissue and is the cause of worsening dyspnea (shortness of breath). IPF is usually associated with a poor prognosis with a median survival time of 2-3 years after diagnosis. IPF is believed to be the result of an aberrant wound healing process including/involving abnormal and excessive deposition of collagen (fibrosis) in the pulmonary interstitium with minimal associated inflammation (Harari S, Caminati A (2010). "IPF: new insight on pathogenesis and treatment". Allergy. 65 (5): 537-553).

Fibroblasts play a central role in the pathogenesis of fibrotic processes that are common to ILDs, PF-ILDs and IPF, and several factors influence their proliferation and their extracellular matrix (ECM) synthesis. In ILDs, these mesenchymal cells have an increased activity with respect to proliferation, migration, extracellular matrix (ECM) synthesis and response to fibrogenic cytokines. The increased deposition of ECM from activated fibroblasts (called "myofibroblasts") contributes to the stiffening of the lung tissue and the destruction of alveolar oxygen exchange area which results in progressive dyspnea and eventually death.

Based on the similarity in both the underlying pathophysiology and clinical course of PF-ILD and IPF, it is anticipated that therapeutically active agents which target fundamental processes in progressive lung fibrosis in IPF will elicit comparable therapeutic effects in PF-ILD.

In 2014, the US Food and Drug Administration (FDA) approved the first drugs for the treatment of IPF in the US: Nintedanib (OFEV) by Boehringer Ingelheim Pharmaceuticals Inc. and Pirfenidone (ESBRIET) by InterMune Inc. Pirfenidone had already been approved for the treatment of IPF in Europe, Japan and several other countries at that time and Nintedanib was approved as a treatment for IPF in Europe in January 2015.

Consequently, the standard treatments of IPF today are either Pirfenidone treatment (U.S. Pat. No. 3,974,281 B) or Nintedanib treatment (U.S. Pat. No. 6,762,180 B; P05-1275) (https://consultqd.clevelandclinic.org/2015/09/pirfenidone-and-nintedanib-novel-agents-in-the-treatment-of-idiopathic-pulmonary-fibrosis/).

However, in patients with IPF having a mild or moderate impairment of FVC (≥50% predicted), both presently approved medicaments Pirfenidone and Nintedanib, can only reduce the decline in FVC, consistent with a slowing of disease progression, but both are not able to stop or even reverse or heal the symptoms of IPF (Tzouvelekis et al Ther. Clin. Risk Management 2015, 11, 359-370).

Nevertheless, both treatment-options, either with Pirfenidone or with Nintedanib, show significant beneficial effects in slowing down IPF disease progression.

The most prominent side effects associated with both, Nintedanib and Pirfenidone, are gastrointestinal events, particularly diarrhea, nausea, vomiting, abdominal pain, decreased appetite and a decreased body weight. In case that gastrointestinal side effects arise, they are usually managed either by treatment interruption, dose reduction or symptomatic treatment of the gastrointestinal side effects (see Mazzei et al, Ther. Adv. Respir. Dis. 2015, Vol. 9 [3], pp. 121-129).

Due to these "accumulative gastrointestinal side effects" of Pirfenidone on the one hand and of Nintedanib on the other hand a combination treatment for IPF by a combination of Pirfenidone and Nintedanib is not frequently used. Investigations have shown that a combination treatment with Pirfenidone and Nintedanib leads to increased gastrointestinal side effects, in particular to diarrhoea, nausea, vomiting, and upper abdominal pain (Vancheri et al., Nintedanib with Add-on Pirfenidone in Idiopathic Pulmonary Fibrosis: Results of the INJOURNEY Trial. Am J Respir Crit Care Med. 2017, Epub ahead of print).

Consequently, due to the fact that both active agents which are so far approved for the treatment for IPF, Pirfenidone and Nintedanib, are—when administered alone—not able to stop or to heal IPF, but instead can only slow down the IPF disease progression to a certain percentage (Tzouvelekis et al Ther. Clin. Risk Management 2015, 11, 359-370), and due to the fact that additionally both Nintedanib and Pirfenidone show significant gastrointestinal side effects which accumulate when both compounds are combined, there is still a significant medical need for improved medicaments for IPF treatment/PF-ILD treatment, in particular for improved combination treatments/combination medicaments comprising as a first combination partner either one of the approved medicaments in IPF Nintedanib or Pirfenidone (with proven efficacy in IPF treatment) and a second other suitable combination partner which is active in IPF/PF-ILD treatment with acceptable tolerability (but which is different from Pirfenidone or Nintedanib). Hereby, it would be extraordinarily beneficial to provide a new medicament combination with a good/improved therapeutic efficacy and with an acceptable tolerability, in particular with regard to gastrointestinal side effects.

Consequently, it was the problem of the instant invention to provide a new combination treatment/combination medicament for PF-ILD treatment/IPF treatment, comprising as a first combination partner one of the presently approved medicaments in IPF, either Nintedanib or Pirfenidone, and a second combination partner (which is different from Nintedanib or Pirfenidone), whereby this combination treatment/combination medicament is improved compared to the PF-ILD/IPF treatment with the first combination partner alone.

This problem was solved by providing a combination treatment/combination medicament for PF-ILD treatment/IPF treatment, comprising as a first combination partner a therapeutically effective amount of Nintedanib or a pharmaceutically acceptable salt thereof and as a second combination partner a therapeutically effective amount of a PDE4B-inhibitor of formula I

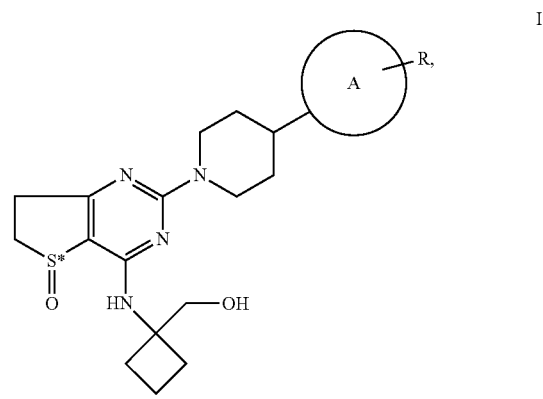

wherein Ring A is a 6-membered aromatic ring which may optionally comprise one or two nitrogen atoms and wherein R is Cl and wherein R may be located either in the para-, meta- or ortho-position of Ring A, wherein S* is a sulphur atom that represents a chiral center or a pharmaceutically acceptable salt thereof.

Hereby the second combination partner is preferably a therapeutically effective amount of a PDE4B-inhibitior of formula II

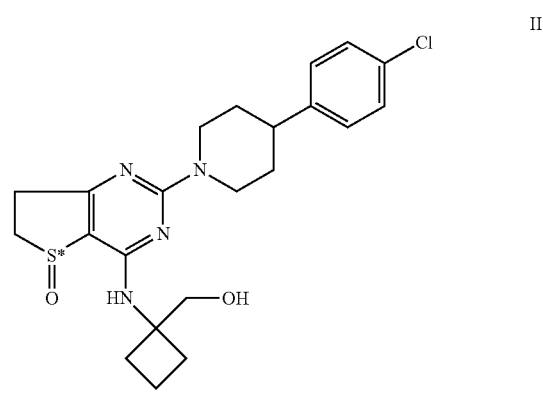

or of formula III

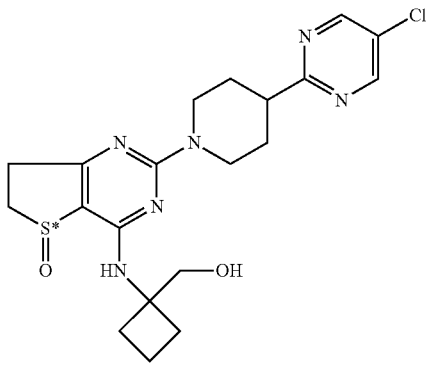

or a pharmaceutically acceptable salts thereof,
more preferably the second combination partner is a PDE4B-inhibitor of formula III

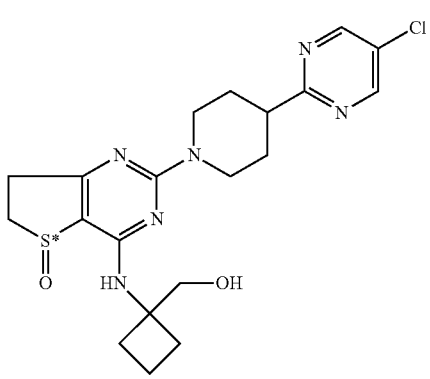

or a pharmaceutically acceptable salts thereof.

This above-mentioned new combination treatment/combination medicament for PF-ILD treatment/IPF treatment, comprising as a first combination partner Nintedanib and as a second combination partner a PDE4B-inhibitor of formula I, preferably a PDE4B-inhibitor of either formula II or III, particularly a PDE4B-inhibitor of either formula III, shows an improved therapeutic efficacy in PF-ILD/IPF-treatment compared to treatment with Nintedanib alone or compared to treatment with the above PDE4B-inhibitor alone.

Experiments A) and B) as described in Chapter 6 (Experimental Data) have experimentally shown that the combination comprising the PDE4B-inhibitor of formula III and Nintedanib shows a) a clear inhibitory effect on the "fibroblast to myofibroblast transition" (which corresponds to the "second level of pathogenesis of fibrotic processes common to PF-ILDs", whereas Nintedanib (an already approved medicament for IPF treatment) shows no corresponding inhibitory effect on the "fibroblast to myofibroblast transition" (consequently the PDE4B-inhibitor of formula III shows a "complementary therapeutic effect" to Nintedanib which indicates that a combination of the PDE4B-inhibitor of formula III and Nintedanib should have a strong advantage over the treatment with Nintedanib alone) and b) a clear "overadditive synergistic inhibitory effect" on "fibroblast proliferation" (which corresponds to the "third level of pathogenesis of fibrotic processes common to PF-ILDs" which the tested other PDE4-inhibitor/Nintedanib combinations Roflumilast/Nintedanib and Apremilast/Nintedanib surprisingly did not show).

This above-mentioned combination treatment/combination medicament for PF-ILD treatment, particularly for IPF-treatment, of the invention comprising as a first combination partner Nintedanib and as a second new combination partner a PDE4B-inhibitor of formula I, preferably a PDE4B-inhibitor of either formula II or III, particularly a PDE4B-inhibitor of formula III, further shows an acceptable tolerability in PF-ILD-treatment.

"Acceptable tolerability" means in this context that the tolerability of the treatment with the combination of Nintedanib with the PDE4B-inhibitor of formula I, preferably of formulas II and III, particularly of formula III, is better than the tolerability of the combination Nintedanib and Pirfenidone, preferably only slightly worse, more preferable not significantly worse compared to treatment with Nintedanib alone and should therefore be well-tolerated by the patient.

Nintedanib, the compound of formula A (free base),

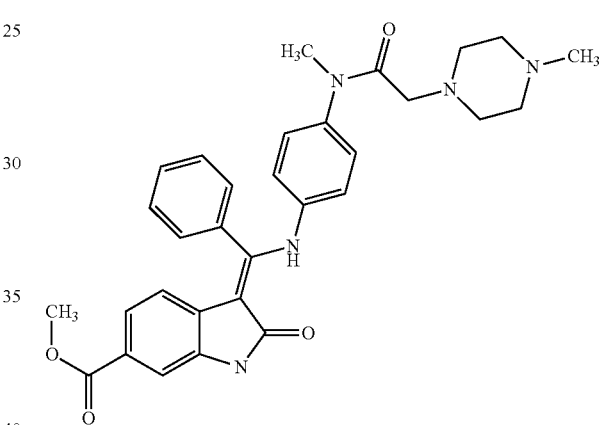

is described in U.S. Pat. No. 6,762,180 B1 (WO 01/27081) which is hereby incorporated by reference.

U.S. Pat. No. 7,119,093B (WO 2004/013099) discloses the monoethanesulphonate salt of this compound of formula A; further salt forms are presented in US 2009/0318471 A (WO 2007/141283).

Both, U.S. Pat. No. 7,119,093B and US 2009/0318471 A are hereby incorporated by reference.

Nintedanib is a highly potent, orally bioavailable inhibitor of vascular endothelial growth factor receptors (VEGFRs), platelet-derived growth factor receptors (PDGFRs) and fibroblast growth factor receptors (FGFRs). It binds competitively to the adenosine triphosphate (ATP) binding pocket of these receptors and blocks intracellular signalling. In addition, Nintedanib inhibits Fms-like tyrosine-protein kinase 3 (Flt 3), lymphocyte-specific tyrosine-protein kinase (Lck), tyrosine-protein kinase lyn (Lyn) and proto-oncogene tyrosine-protein kinase src (Src) (Hilberg et al., Cancer Res. 2008, 68, 4774-4782). Recently, it was discovered that nintedanib also inhibits colony stimulating factor 1 receptor (CSF1R) (Tandon et al., Am J Respir Crit Care Med 2017; 195:A2397).

Nintedanib was shown to be able to inhibit or attenuate cellular proliferation, contributing to angiogenesis (Hilberg et al., Cancer Res. 2008, 68, 4774-4782), as well as lung fibroblast proliferation, migration (Hostettler et al., Respir Res. 2014, 15, 157) and transformation to myofibroblasts (Wollin et al., Eur. Respir J 2015, 45, 1434-1445.) contributing to lung fibrosis (e.g. IPF), SSc-ILD and RA-ILD. Furthermore, it revealed anti-fibrotic and anti-inflammatory activity in lung fibrosis models (Wollin et al., Eur. Respir J 2015, 45, 1434-1445; Wollin et al., J. Pharmacol. Exp. Ther. 2014, 394, 209-220). Additionally Nintedanib demonstrated the ability to inhibit fibroblast migration, proliferation and transformation to myofibroblasts in SSc cellular models, to attenuate skin and lung fibrosis in SSc and SSc-ILD animal models (Huang et al., Ann. Rheum. Dis. 2016, 74, 883-890, Huang et al., Ann Rheum Dis. 2017, EPub ahead of print), to reduce lung fibrosis in RA-ILD animal models (Redente et al., Am J Respir Crit Care Med 2016, 193, A4170) and to attenuate lung fibrosis in a chronic mouse model of allergic lung impairment resembling aspects of HP (Lee et al. Exp Lung Res. 2017 EPub ahead of print).

Pharmaceutical dosage forms comprising Nintedanib are disclosed in U.S. Pat. No. 9,907,756B (WO 2009/147212) and in US 2011/0190318 (WO 2009/147220) and are herein incorporated per reference. Also, a dry powder formulation for inhalation has been described (Vartiainen et al., poster presentation at the International Colloquium of Lung and Airway Fibrosis in Dublin, September 2016).

The use of Nintedanib for the treatment of a large variety of diseases, between many others also the use for the treatment of fibrotic diseases is described in WO 2006/067165.

Nintedanib as a single treatment for idiopathic pulmonary fibrosis is usually dosed twice daily with 150 mg (twice daily with 100 mg for patients with mild hepatic impairment).

Further, WO 2006/067165 discloses that Nintedanib may be combined with a large variety of different combination partners. Between many other combinations partners WO 2006/067165 also proposes to combine Nintedanib with PDE4-inhibitors such as for example Roflumilast.

However, in contrast to Nintedanib (which has been approved for the treatment of IPF in the meantime) the PDE4-inhibitor Roflumilast (originally disclosed in U.S. Pat. No. 5,712,298 B) has never been neither developed nor approved for the treatment of proliferative fibrotic diseases such as PF-ILD or IPF in particular. Instead, Roflumilast was in the meantime approved for the treatment of chronic obstructive pulmonary disease (COPD) only which is a respiratory disease that does not involve any fibrotic symptoms. Also other PDE4-inhibitors such as for example Apremilast (originally disclosed in U.S. Pat. No. 6,020,358B) that appeared on the market in the following years have never been considered for being developed or for being approved for the treatment of proliferative fibrotic diseases such as PF-ILD or for IPF in particular, but instead Apremilast was approved for the treatment of psoriasis only (a skin disease).

Additionally to Roflumilast and Apremilast-many further patent applications drawn on other PDE4/PDE4B-inhibitors with improved properties were published:

Pteridines as PDE4-inhibitors in WO 2006/056607, WO 2006/058869, WO 2006/058868 and WO 2006/058867.

Piperazino-Dihydrothienopyrimidines as PDE4-inhibitors in WO 2006/111549, WO 2007/118793 and WO 2009/050242.

Piperidino-Dihydrothienopyrimidines as PDE4B-inhibitors in WO 2009/050248 and in WO 2013/026797.

The PDE4B-inhibitors of formula I

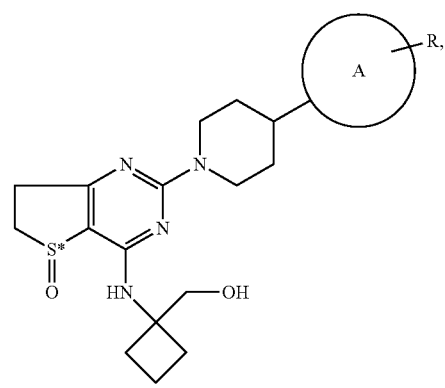

wherein Ring A is a 6-membered aromatic ring which may optionally comprise one or two nitrogen atoms and wherein R is Cl and wherein R may be located either in the para-, meta- or ortho-position of Ring A, wherein S* is a sulphur atom that represents a chiral center, in particular the PDE4B-inhibitors of formula II

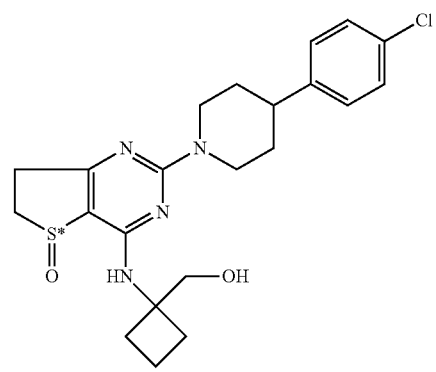

and of formula III

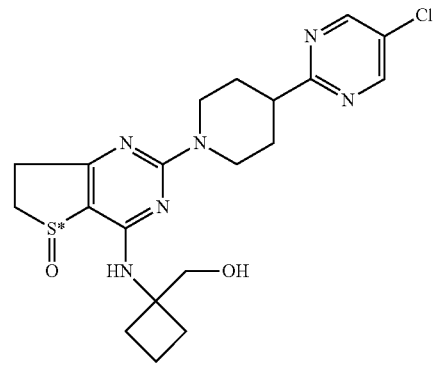

have been disclosed in U.S. Pat. No. 8,609,670B (WO 2013/026797) which is hereby incorporated by reference.

2. GENERAL TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The terms "treatment" and "treating" as used herein embrace both therapeutic, i.e. curative and/or palliative, and preventive, i.e. prophylactic, treatment.

Therapeutic treatment refers to the treatment of patients having already developed one or more of said conditions in manifest, acute or chronic form. Therapeutic treatment may be symptomatic treatment in order to relieve the symptoms of the specific indication or causal treatment in order to reverse or partially reverse the conditions of the indication or to stop or slow down progression of the disease.

Preventive treatment ("prevention") refers to the treatment of patients at risk of developing one or more of said conditions, prior to the clinical onset of the disease in order to reduce said risk.

The terms "treatment" and "treating" include the administration of one or more active compounds in order to prevent or delay the onset of the symptoms or complications and to prevent or delay the development of the disease, condition or disorder and/or in order to eliminate or control the disease, condition or disorder as well as to alleviate the symptoms or complications associated with the disease, condition or disorder.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

3. DETAILED DESCRIPTION OF THE INVENTION

The instant application refers to a method of treating one or more Progressive Fibrosing Interstitial Lung Diseases (PF-ILDs)), comprising administering to a patient in need thereof a therapeutically effective amount of a PDE4B-inhibitor of formula I

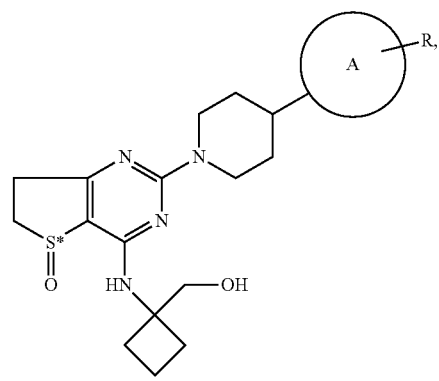

wherein Ring A is a 6-membered aromatic ring which may optionally comprise one or two nitrogen atoms and wherein R is Cl and wherein R may be located either in the para-, meta- or ortho-position of Ring A, wherein S* is a sulphur atom that represents a chiral center or a pharmaceutically acceptable salt thereof and a therapeutically effective amount of a tyrosine kinase inhibitor selected from the group consisting of Nintedanib and a pharmaceutically acceptable salt thereof.

In a preferred embodiment of the above-mentioned method said PDE4B-inhibitor of formula I is administered in a dose that will lead to an estimated human free fraction of the compound of formula I between 1 nMol/L to 2000 nMol/L, more preferred between 1 nMol/L to 1000 nMol/L.

In a preferred embodiment of the above-mentioned method the Progessive Fibrosing Interstitial Lung Disease is Idiopathic Pulmonary Fibrosis (IPF) or systemic Sclerosis ILD (SSc-ILD).

In another preferred embodiment of the above-mentioned method the above-mentioned PDE4B-inhibitor of formula I is administered simultaneously, concurrently, sequentially, successively, alternately or separately with the tyrosine kinase inhibitor selected from the group consisting of Nintedanib and a pharmaceutically acceptable salt thereof.

In a further preferred embodiment of the above-mentioned method said tyrosine kinase inhibitor is Nintedanib in the form of its monoethanesulfonate.

In another further preferred embodiment of the above-mentioned method said tyrosine kinase inhibitor is Nintedanib in the form of its monoethanesulfonate and is administered in a dose that will lead to an estimated human free fraction of Nintedanib monoethanesulfonate between 1 nMol/L to 300 nMol/L, more preferred between 10 nMol/L to 100 nMol/L.

In a more preferred embodiment of the above-mentioned method said PDE4B-inhibitor of formula I is selected from the group consisting of the compound of formula II

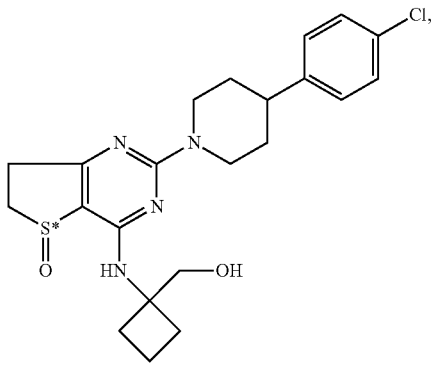

a pharmaceutically acceptable salt thereof,
the compound of formula III

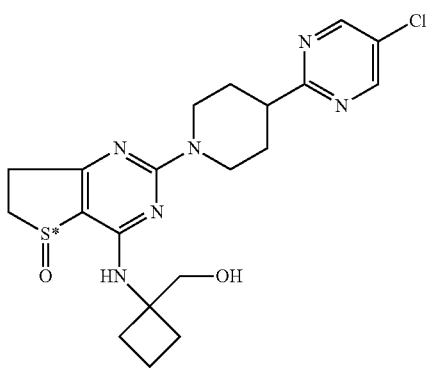

or a pharmaceutically acceptable salt thereof.

In a particularly preferred embodiment of the above-mentioned method said PDE4B-inhibitor of formula I is the compound of formula III

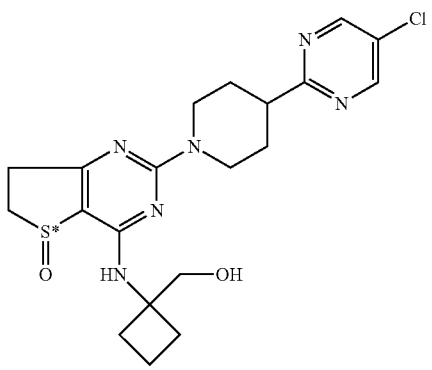

or a pharmaceutically acceptable salt thereof.

In another particularly preferred embodiment of the above-mentioned method said PDE4B-inhibitor of formula I is the compound of formula III and is administered in a dose that will lead to an estimated human free fraction of the compound of formula III between 1 nMol/L to 2000 nMol/L, more preferred between 1 nMol/L to 1000 nMol/L.

Furthermore, the instant application refers to a PDE4B-inhibitor of formula I

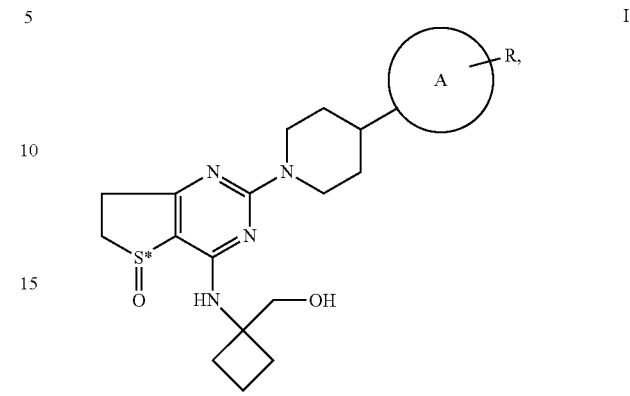

wherein Ring A is a 6-membered aromatic ring which may optionally comprise one or two nitrogen atoms and wherein R is Cl and wherein R may be located either in the para-, meta- or ortho-position of Ring A, wherein S* is a sulphur atom that represents a chiral center or a pharmaceutically acceptable salt thereof, for use in a method of treating one or more Progressive Fibrosing Interstitial Lung Diseases (PF-ILDs) said method comprising administering to a patient in need thereof a therapeutically effective amount of said PDE4B-inhibitor of formula I in combination with a therapeutically effective amount of a tyrosine kinase inhibitor selected from the group consisting of Nintedanib and a pharmaceutically acceptable salt thereof.

In a preferred embodiment the above-identified Progessive Fibrosing Interstitial Lung Disease (PF-ILD) is either idiopathic pulmonary fibrosis (IPF) or systemic sclerosis ILD (SSC-ILD), more preferred IPF.

In another preferred embodiment the above-mentioned PDE4B-inhibitor of formula I is administered simultaneously, concurrently, sequentially, successively, alternately or separately with the tyrosine kinase inhibitor selected from the group consisting of Nintedanib and a pharmaceutically acceptable salt thereof.

In a further preferred embodiment the above-mentioned tyrosine kinase inhibitor is Nintedanib in the form of its monoethanesulfonate.

In another further preferred embodiment the above-mentioned tyrosine kinase inhibitor is Nintedanib in the form of its monoethanesulfonate and is administered in a dose that will lead to an estimated human free fraction of Nintedanib monoethanesulfonate between 1 nMol/L to 300 nMol/L, more preferred between 10 nMol/L to 100 nMol/L.

In a more preferred embodiment the above-mentioned PDE4B-inhibitor of formula I is selected from the group consisting of the compound of formula II

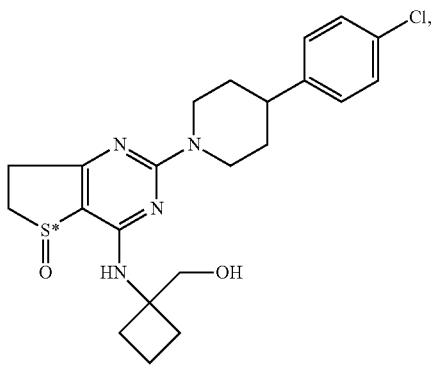

a pharmaceutically acceptable salt thereof, the compound of formula III

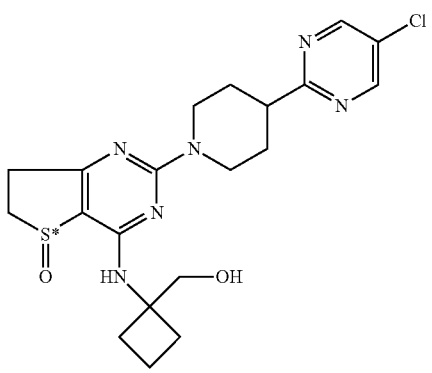

and a pharmaceutically acceptable salt thereof.

In a particularly preferred embodiment the above-mentioned PDE4B-inhibitor of formula I is the compound of formula III

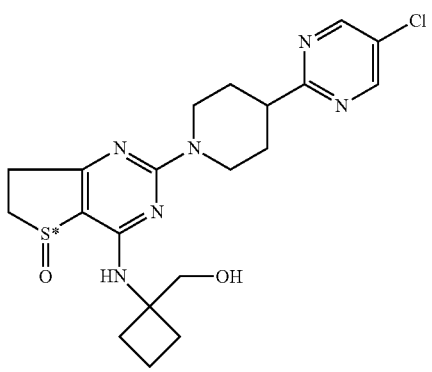

or a pharmaceutically acceptable salt thereof.

In another particularly preferred embodiment the above-mentioned PDE4B-inhibitor of formula I is the compound of formula III and is administered in a dose that will lead to an estimated human free plasma fraction of the compound of formula III between 1 nMol/L to 2000 nMol/L, more preferred between 1 nMol/L to 1000 nMol/L.

Further, the instant application refers to a tyrosine kinase inhibitor selected from the group consisting of Nintedanib and pharmaceutically acceptable salts thereof for use in a method of treating one or more Progressive Fibrosing Interstitial Lung Diseases (PF-ILDs), said method comprising administering to a patient in need thereof a therapeutically effective amount of said tyrosine kinase inhibitor in combination with a therapeutically effective amount of a PDE4B-inhibitor of formula I

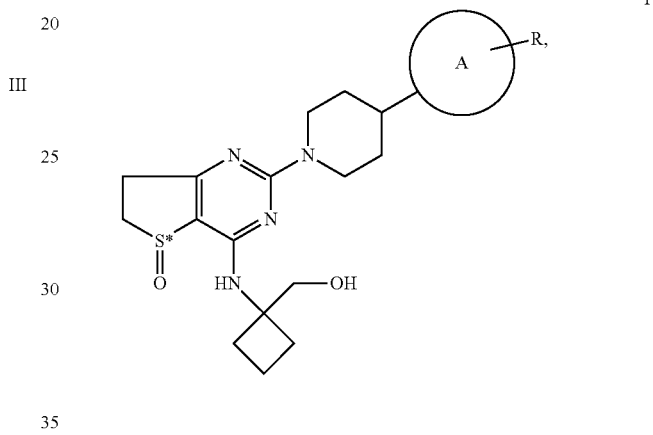

wherein Ring A is a 6-membered aromatic ring which may optionally comprise one or two nitrogen atoms and wherein R is Cl and wherein R may be located either in the para-, meta- or ortho-position of Ring A, wherein S* is a sulphur atom that represents a chiral center or a pharmaceutically acceptable salt thereof.

In a preferred embodiment the above one or more Progressive Fibrosing Interstitial Lung Diseases (PF-ILDs) will be either idiopathic pulmonary fibrosis (IPF) or systemic sclerosis ILD (SSC-ILD, more preferred IPF.

In another preferred embodiment the above-mentioned tyrosine kinase inhibitor is administered simultaneously, concurrently, sequentially, successively, alternately or separately with the PDE4B-inhibitor of formula I.

In a further preferred embodiment the above-mentioned tyrosine kinase inhibitor is Nintedanib in the form of its monoethanesulfonate.

In another further preferred embodiment the above-mentioned method tyrosine kinase inhibitor is Nintedanib in the form of its monoethanesulfonate and is administered in a dose that will lead to an estimated human free fraction of Nintedanib monoethanesulfonate between 1 nMol/L to 300 nMol/L, more preferred between 10 nMol/L to 100 nMol/L.

In a more preferred embodiment the above-mentioned PDE4B-inhibitor of formula I is selected from the group consisting of the compound of formula II

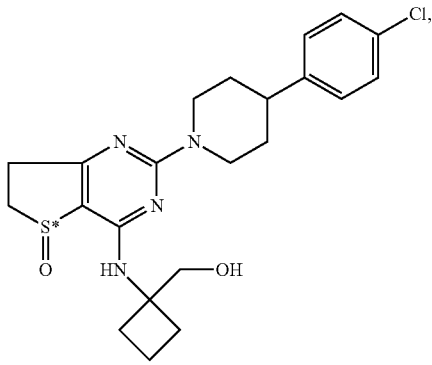

II a pharmaceutically acceptable salt thereof, the compound of formula III

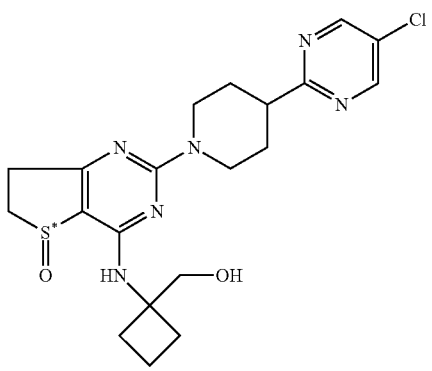

III and a pharmaceutically acceptable salt thereof.

In a particularly preferred embodiment the above-mentioned PDE4B-inhibitor of formula I is the compound of formula III

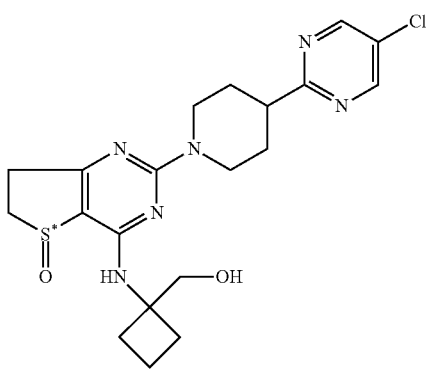

III or a pharmaceutically acceptable salt thereof.

The instant application refers to the use of a PDE4B-inhibitor of formula I

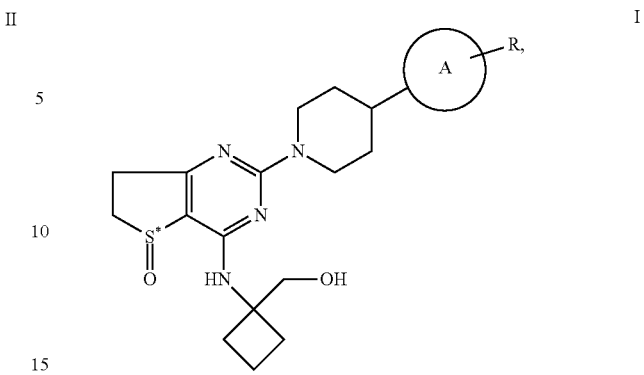

I wherein Ring A is a 6-membered aromatic ring which may optionally comprise one or two nitrogen atoms and wherein R is Cl and wherein R may be located either in the para-, meta- or ortho-position of Ring A, wherein S* is a sulphur atom that represents a chiral center or of a pharmaceutically acceptable salt thereof for preparing a pharmaceutical composition for use in a method of treating one or more Progressive Fibrosing Interstitial Lung Diseases (PF-ILDs), wherein a therapeutically effective amount of said PDE4B-inhibitor of formula I or a pharmaceutically acceptable salt thereof is to be administered to a patient in need thereof in combination with a therapeutically effective amount of a tyrosine kinase inhibitor selected from the group consisting of Nintedanib and a pharmaceutically acceptable salt thereof.

In a preferred embodiment the application refers to the above-mentioned use of a PDE4B-inhibitor of formula I for preparing a pharmaceutical composition for use in a method of treating one or more Progressive Fibrosing Interstitial Lung Diseases (PF-ILDs), wherein said Progessive Fibrosing Interstitial Lung Disease is either idiopathic pulmonary fibrosis (IPF) or systemic sclerosis ILD (SSC-ILD), more preferred IPF.

In a further preferred embodiment the application refers to the above-mentioned use of a PDE4B-inhibitor of formula I for preparing a pharmaceutical composition for use in a method of treating one or more Progressive Fibrosing Interstitial Lung Diseases (PF-ILDs), wherein said PDE4B-inhibitor of formula I is to be administered simultaneously, concurrently, sequentially, successively, alternately or separately with the tyrosine kinase inhibitor selected from the group consisting of Nintedanib and a pharmaceutically acceptable salt thereof.

In another preferred embodiment the application refers to the above-mentioned use of a PDE4B-inhibitor of formula I for preparing a pharmaceutical composition for use in a method of treating one or more Progressive Fibrosing Interstitial Lung Diseases (PF-ILDs), wherein said tyrosine kinase inhibitor is Nintedanib in the form of its monoethanesulfonate.

In another further preferred embodiment of the above-mentioned use said tyrosine kinase inhibitor is Nintedanib in the form of its monoethanesulfonate and is administered in a dose that will lead to an estimated human free fraction of Nintedanib monoethanesulfonate between 1 nMol/L to 300 nMol/L, more preferred between 10 nMol/L to 100 nMol/L.

In a more preferred embodiment the application refers to the above-mentioned use of a PDE4B-inhibitor of formula I for preparing a pharmaceutical composition for use in a method of treating one or more Progressive Fibrosing Interstitial Lung Diseases (PF-ILDs), wherein said PDE4B-inhibitor of formula I is selected from the group consisting of the compound of formula II

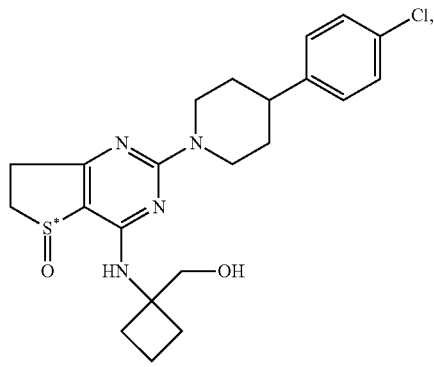

a pharmaceutically acceptable salt thereof, the compound of formula III

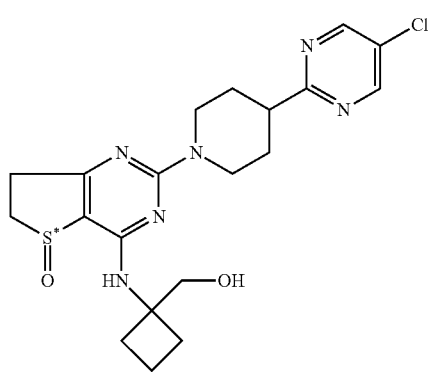

and a pharmaceutically acceptable salt thereof.

In a particularly preferred embodiment the application refers to the above-mentioned use of a PDE4B-inhibitor of formula I for preparing a pharmaceutical composition for use in a method of treating one or more Progressive Fibrosing Interstitial Lung Diseases (PF-ILDs), wherein said PDE4B-inhibitor of formula I is the compound of formula III

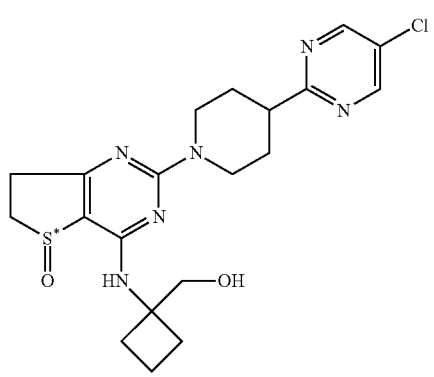

or a pharmaceutically acceptable salt thereof.

In another particularly preferred embodiment the application refers to the above-mentioned use for preparing a pharmaceutical composition for use in a method of treating one or more Progressive Fibrosing Interstitial Lung Diseases (PF-ILDs), wherein the PDE4B-inhibitor of formula I is the compound of formula III and is administered in a dose that will lead to an estimated human free plasma fraction of the compound of formula III between 1 nMol/L to 2000 nMol/L, more preferred between 1 nMol/L to 1000 nMol/L.

The instant application refers to the use of a tyrosine kinase inhibitor selected from the group consisting of Nintedanib and a pharmaceutically acceptable salt thereof for preparing a pharmaceutical composition for use in a method of treating one or more Progressive Fibrosing Interstitial Lung Diseases (PF-ILDs), wherein a therapeutically effective amount of said tyrosine kinase inhibitor is to be administered to a patient in need thereof in combination with a therapeutically effective amount of the PDE4B-inhibitor of formula I

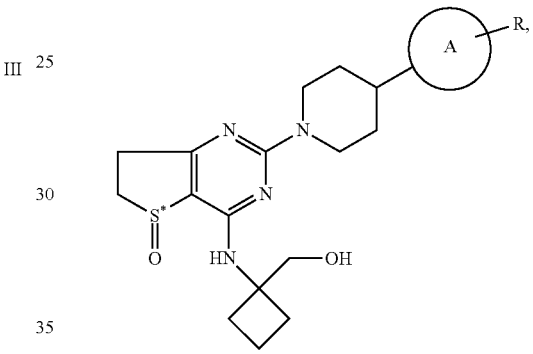

wherein Ring A is a 6-membered aromatic ring which may optionally comprise one or two nitrogen atoms and wherein R is Cl and wherein R may be located either in the para-, meta- or ortho-position of Ring A, wherein S* is a sulphur atom that represents a chiral center or a pharmaceutically acceptable salt thereof.

In a preferred embodiment the application refers to the above-mentioned use of the tyrosine kinase inhibitor selected from the group consisting of Nintedanib and a pharmaceutically acceptable salt thereof for preparing a pharmaceutical composition for use in a method of treating one or more Progressive Fibrosing Interstitial Lung Diseases (PF-ILDs), wherein said Progessive Fibrosing Interstitial Lung Disease is either Idiopathic Pulmonary Fibrosis (IPF) or systemic sclerosis ILD (SSC-ILD), more preferred IPF.

In a further preferred embodiment the application refers to the above-mentioned use of the tyrosine kinase inhibitor selected from the group consisting of Nintedanib and a pharmaceutically acceptable salt thereof for preparing a pharmaceutical composition for use in a method of treating one or more Progressive Fibrosing Interstitial Lung Diseases (PF-ILDs), wherein said tyrosine kinase inhibitor is to be administered simultaneously, concurrently, sequentially, successively, alternately or separately with the PDE4B inhibitor of formula I or a pharmaceutically acceptable salt thereof.

In another preferred embodiment the application refers to the above-mentioned use of the tyrosine kinase inhibitor selected from the group consisting of Nintedanib and a pharmaceutically acceptable salt thereof for preparing a pharmaceutical composition for use in a method of treating one or more Progressive Fibrosing Interstitial Lung Diseases (PF-ILDs), wherein said tyrosine kinase inhibitor is Nintedanib in the form of its monoethanesulfonate.

In another further preferred embodiment of the above-mentioned use said tyrosine kinase inhibitor is Nintedanib in the form of its monoethanesulfonate and is administered in a dose that will lead to an estimated human free fraction of Nintedanib monoethanesulfonate between 1 nMol/L to 300 nMol/L, more preferred between 10 nMol/L to 100 nMol/L.

In a more preferred embodiment the application refers to the above-mentioned use of the tyrosine kinase inhibitor selected from the group consisting of Nintedanib and a pharmaceutically acceptable salt thereof for preparing a pharmaceutical composition for use in a method of treating one or more Progressive Fibrosing Interstitial Lung Diseases (PF-ILDs), wherein said PDE4B-inhibitor of formula I is selected from the group consisting of the compound of formula II

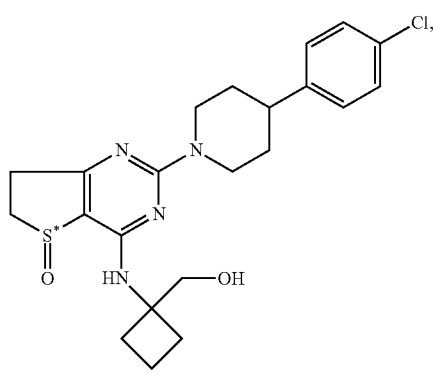

II a pharmaceutically acceptable salt thereof,
the compound of formula III

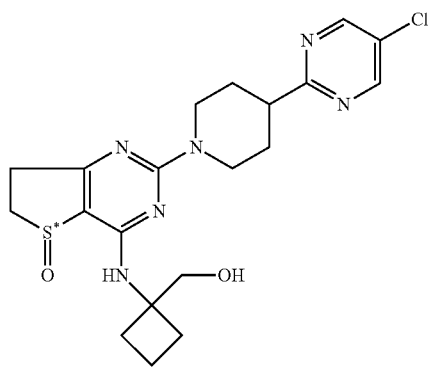

III and a pharmaceutically acceptable salt thereof.

In a particularly preferred embodiment the application refers to the use of a tyrosine kinase inhibitor selected from the group consisting of Nintedanib and a pharmaceutically acceptable salt thereof for preparing a pharmaceutical composition for use in a method of treating one or more Progressive Fibrosing Interstitial Lung Diseases (PF-ILDs), wherein said PDE4B-inhibitor of formula I is the compound of formula III

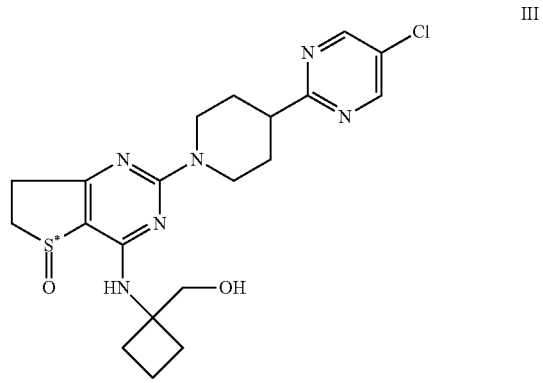

III or a pharmaceutically acceptable salt thereof.

In another particularly preferred embodiment the application refers to the above-mentioned use of a tyrosine kinase inhibitor for preparing a pharmaceutical composition for use in a method of treating one or more Progressive Fibrosing Interstitial Lung Diseases (PF-ILDs), wherein the PDE4B-inhibitor of formula I is the compound of formula III and is administered in a dose that will lead to an estimated human free plasma fraction of the compound of formula III between 1 nMol/L to 2000 nMol/L, more preferred between 1 nMol/L to 1000 nMol/L.

In another embodiment the instant application refers to a pharmaceutical composition comprising:
a PDE4B-inhibitor of formula I

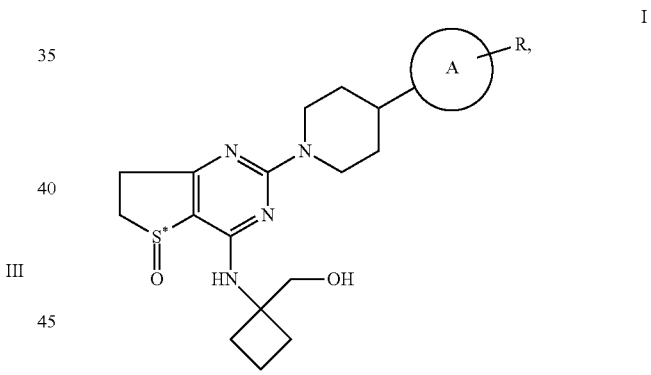

I wherein Ring A is a 6-membered aromatic ring which may optionally comprise one or two nitrogen atoms and
wherein R is Cl and
wherein R may be located either in the para-, meta- or ortho-position of Ring A,
wherein S* is a sulphur atom that represents a chiral center
or a pharmaceutically acceptable salt thereof
a tyrosine kinase inhibitor selected from the group consisting of Nintedanib and a pharmaceutically acceptable salt thereof, and
optionally, one or more pharmaceutically acceptable carriers and/or excipients.

In a preferred embodiment the application refers to the above-mentioned pharmaceutical composition, wherein said tyrosine kinase inhibitor is Nintedanib in the form of its monoethanesulfonate.

In another further preferred embodiment of the above-mentioned pharmaceutical composition said tyrosine kinase inhibitor is Nintedanib in the form of its monoethanesulfonate and is administered in a dose that will lead to an estimated human free fraction of Nintedanib monoethanesulfonate between 1 nMol/L to 300 nMol/L, more preferred between 10 nMol/L to 100 nMol/L.

In a preferred embodiment the instant application refers to the above-mentioned pharmaceutical composition, wherein said PDE4-B-inhibitor of formula I is selected from the group consisting of the compound of formula II

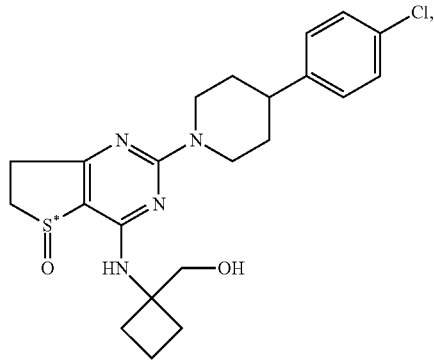

a pharmaceutically acceptable salt thereof,
the compound of formula III

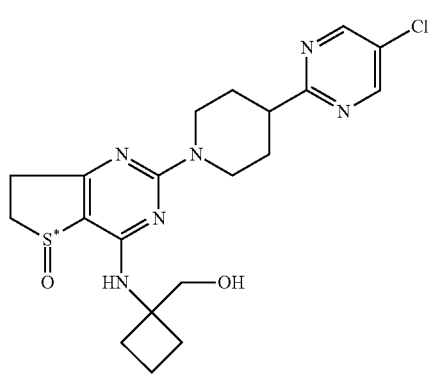

and a pharmaceutically acceptable salt thereof.

In a particularly preferred embodiment the instant application refers to the above-mentioned pharmaceutical composition, wherein said PDE4-B-inhibitor of formula I is the compound of formula III

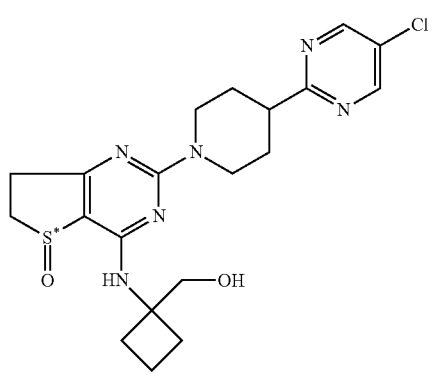

or a pharmaceutically acceptable salt thereof.

In another particularly preferred embodiment the instant application refers to the above-mentioned pharmaceutical composition, wherein said PDE4-B-inhibitor of formula I is the compound of formula III in a dose that leads to an estimated human free plasma fraction of the compound of formula III between 1 nMol/L and 2000 nMol/L, preferably between 1 nMol/L and 1000 nMol/L.

In a further embodiment the instant application refers to a kit comprising:
a first pharmaceutical composition or dosage form comprising a PDE4B-inhibitor of formula I

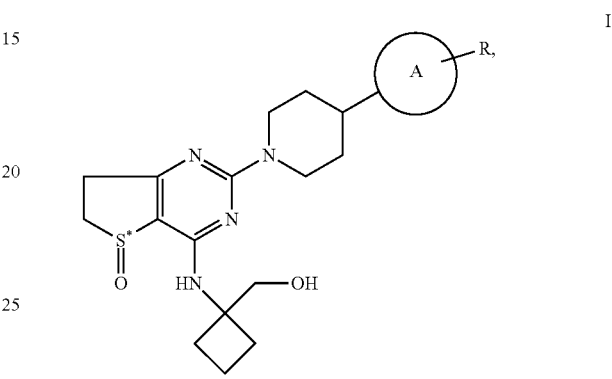

wherein Ring A is a 6-membered aromatic ring which may optionally comprise one or two nitrogen atoms and
wherein R is Cl and
wherein R may be located either in the para-, meta- or ortho-position of Ring A,
wherein S* is a sulphur atom that represents a chiral center
or a pharmaceutical acceptable salt thereof, and optionally, one or more pharmaceutically acceptable carriers and/or excipients and
a second pharmaceutical composition or dosage form comprising a tyrosine kinase inhibitor selected from the group consisting of Nintedanib and a pharmaceutically acceptable salt thereof, and optionally, one or more pharmaceutically acceptable carriers and/or excipients.

In a preferred embodiment the application refers to the above-identified kit is for use in a method of treating one or more Progressive Fibrosing Interstitial Lung Diseases (PF-ILDs).

In a more preferred embodiment the application refers to the above-identified kit is for use in a method of treating either idiopathic pulmonary fibrosis (IPF) or systemic sclerosis ILD (SSc-ILD).

In another preferred embodiment the application refers to the above-identified kit is for use in a method of treating one or more PF-ILDs, wherein said first pharmaceutical composition or dosage form is to be administered simultaneously, concurrently, sequentially, successively, alternately or separately with the second pharmaceutical composition or dosage form.

In a further preferred embodiment the application refers to above-identified kit, wherein said tyrosine kinase inhibitor of the second pharmaceutical composition or dosage form is Nintedanib in the form of its monoethanesulfonate.

In another further preferred embodiment the above-mentioned kit said tyrosine kinase inhibitor is Nintedanib in the form of its monoethanesulfonate and is administered in a dose that will lead to an estimated human free fraction of Nintedanib monoethanesulfonate between 1 nMol/L to 300 nMol/L, more preferred between 10 nMol/L to 100 nMol/L.

In a more preferred embodiment the application refers to above-identified kit, wherein said first pharmaceutical composition or dosage form comprises a PDE4B-inibitor of formula I selected from the group consisting of the compound of formula II

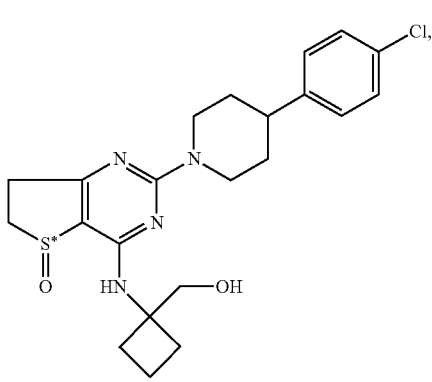

a pharmaceutically acceptable salt thereof,
the compound of formula III

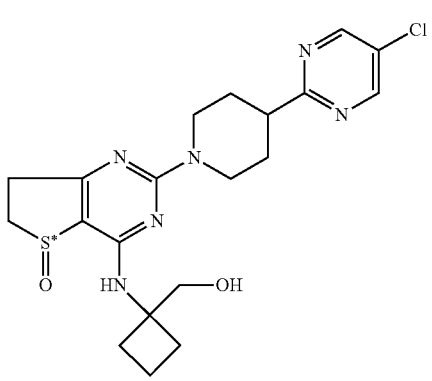

and a pharmaceutically acceptable salt thereof.

In a particularly preferred embodiment the application refers to above-identified kit, wherein said first pharmaceutical composition or dosage form comprises the PDE4B inhibitor compound of formula III

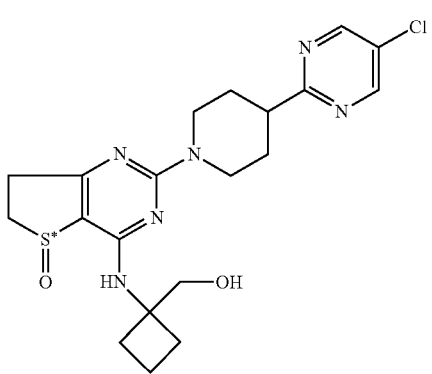

or a pharmaceutically acceptable salt thereof.

In another particularly preferred embodiment the instant application refers to the above-mentioned kit, wherein said PDE4-B-inhibitor of formula I in the first pharmaceutical composition or dosage form is the compound of formula III in a dose that leads to an estimated human free plasma fraction of the compound of formula III between 1 nMol/L and 2000 nMol/L, preferably 1 nMol/L and 1000 nMol/L.

In a particularly preferred embodiment the application refers to any of the above-identified kits, further comprising
a package insert comprising printed instructions for simultaneous, concurrent, sequential, successive, alternate or separate use of the first and the second pharmaceutical composition or dosage forms in the treatment of one or more Progressive Fibrosing Interstitial Lung Diseases (PF-ILDs).

In another particularly preferred embodiment the application refers to any of the above-identified kit, further comprising
a package insert comprising printed instructions for simultaneous, concurrent, sequential, successive, alternate or separate use of the first and the second pharmaceutical composition or dosage forms in the treatment of idiopathic pulmonary fibrosis (IPF).

In another particularly preferred embodiment the application refers to any of the above-identified kit, further comprising
a package insert comprising printed instructions for simultaneous, concurrent, sequential, successive, alternate or separate use of the first and the second pharmaceutical composition or dosage forms in the treatment of systemic sclerosis ILD (SSc-ILD).

4. BRIEF DESCRIPTION OF THE FIGURES

FIG. 1:
Experiment A1):
Concentration—dependent inhibition of TGF-β-stimulated α-SMA protein expression of human lung fibroblasts from patients with IPF by the compound of formula III (filled circles, black line; $IC_{50}$=210 nMol/L) or a combination of the compound of formula III with 100 nMol/L Nintedanib (empty circles, grey line; $IC_{50}$=110 nMol/L).
represents the measured inhibition of α-SMA protein expression of the fibroblasts in the presence of 100 nM Nintedanib alone which showed no inhibitory effect.
Data are presented±SEM of n=5 donors. Data were normalized to untreated (non-stimulated) control cells (=100% inhibition) and to TGF-β-treated cells (=0% inhibition).

Figure 2:
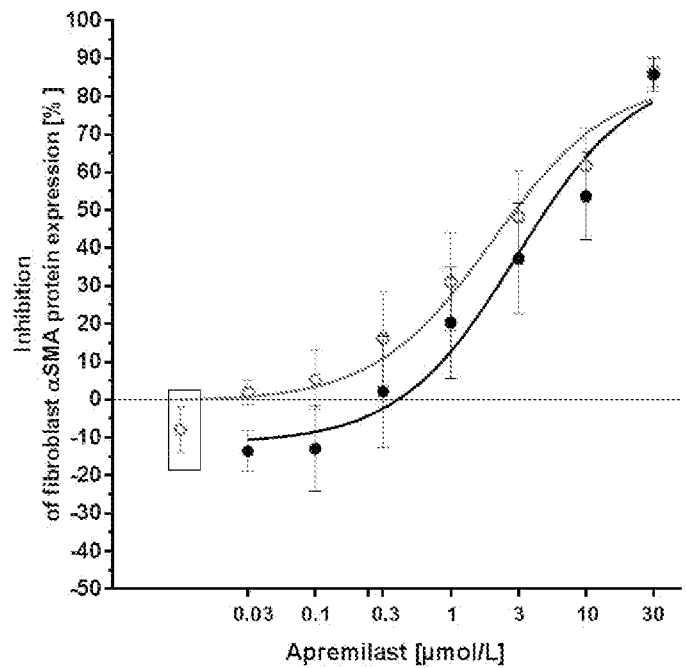

FIG. 2:
Experiment A2):
Concentration—dependent inhibition of TGF-β-stimulated α-SMA protein expression of human lung fibroblasts from patients with IPF by Apremilast (filled circles, black line; $IC_{50}$=3 μMon) or a combination of Apremilast with 100 nMol/L Nintedanib (empty circles, grey line; $IC_{50}$=2 μMon).
represents the measured inhibition of α-SMA protein expression of the fibroblasts in the presence of 100 nM Nintedanib alone which showed no inhibitory effect.
Data are presented±SEM of n=5 donors. Data are normalized to untreated (non-stimulated) control cells (=100% inhibition) and to TGF-β treated cells (=0% inhibition).

Figure 3:
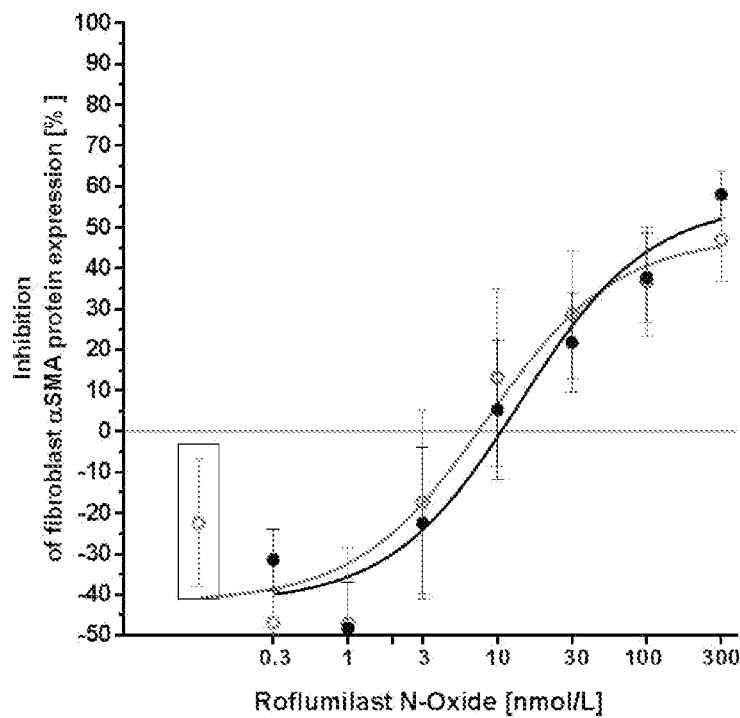

FIG. 3:
Experiment A3):
Concentration—dependent inhibition of TGF-β-stimulated α-SMA protein expression of human lung fibroblasts from patients with IPF by Roflumilast N-Oxide (filled circles, black line; $IC_{50}$=14 nMol/L) or a combination of Roflumilast N-Oxide with 100 nMol/L Nintedanib (empty circles, grey line; $IC_{50}$=8.5 nMol/L).

represents the measured inhibition of α-SMA protein expression of the fibroblasts in the presence of 100 nM Nintedanib alone which showed no inhibitory effect.

Data are presented±SEM of n=5 donors. Data are normalized to untreated (non-stimulated) control cells (=100% inhibition) and TGF-β treated cells (=0% inhibition).

FIG. 4:

Experiment B1):

Concentration—dependent inhibition of FGF plus IL-1β-stimulated proliferation of human lung fibroblasts from patients with IPF by the compound of formula III (filled circles, black solid line; $IC_{50}$=255 nMol/L) or a combination of the compound of formula III with 100 nmol/L Nintedanib (empty circles, grey solid line; $IC_{50}$=23 nMol/L). The calculated additive curve of the combination of both drugs is represented by the empty triangles and the dashed line.

represents the FGF plus IL-1β-stimulated proliferation of human lung fibroblasts from patients with IPF by 100 nM Nintedanib alone.

Data are presented±SEM of n=5 donors. Data are normalized to untreated (non-stimulated) control cells (=100% inhibition) and to FGF+IL-1β treated cells (=0% inhibition).

FIG. 5:

Experiment B2):

Concentration—dependent inhibition of FGF plus IL-1β-stimulated proliferation of human lung fibroblasts from patients with IPF by Apremilast (filled circles, black solid line; $IC_{50}$=1.8 µMol/L) or a combination of Apremilast with 100 nMol/L Nintedanib (empty circles, grey solid line; $IC_{50}$=1.6 µMol/L). The calculated additive curve of the combination of both drugs is represented by the empty triangles and the dashed line.

represents the FGF plus IL-1β-stimulated proliferation of human lung fibroblasts from patients with IPF by 100 nM Nintedanib alone.

Data are presented±SEM of n=5 donors. Data are normalized to untreated (non-stimulated) control cells (=100% inhibition) and to FGF+IL-1β treated cells (=0% inhibition).

FIG. 6:

Experiment B3):

Concentration—dependent inhibition of FGF plus IL-1β-stimulated proliferation of human lung fibroblasts from patients with IPF by Roflumilast N-Oxide (filled circles, black solid line; $IC_{50}$=440 pMol/L) or a combination of Roflumilast N-Oxide with 100 nMol/L Nintedanib (empty circles grey solid line; $IC_{50}$=534 pMol/L).

The calculated additive curve of the combination of both drugs is represented by empty triangles and a dashed line.

represents the FGF plus IL-1β-stimulated proliferation of human lung fibroblasts from patients with IPF by 100 nM Nintedanib alone.

Data are presented±SEM of n=5 donors. Data are normalized to untreated (non-stimulated) control cells (=100% inhibition) and to FGF+IL-1β treated cells (=0% inhibition).

5. EXPERIMENTAL DATA 6.1 Pathogenesis of fibrotic processes that are common to ILDs, PF-ILDs and IPF Pathogenesis of fibrotic processes that are common to ILDs, PF-ILDs and IPF are presently not completely understood.

The main characteristics of IPF are changes in epithelial and mesenchymal cells as well as the interaction between these cells whereas it is currently believed that inflammatory processes play only a minor role [Lehtonen et al, Respiratory Research (2016) 17: 14]. One widely accepted hypothesis to explain the mechanisms in IPF pathogenesis postulates that an injury of the alveolar epithelium results in an excessive wound healing response with overshooting release of growth and transcription factors and cytokines subsequent activation and transformation of fibroblasts to the secreting myofibroblast phenotype resulting in excessive production of extracellular matrix (ECM) proteins, [King T E, Jr, Pardo A, Selman M., .Lancet. 2011; 378:1949-1961]. The fibroblast focus, a typical histological feature of IPF, is a specific aggregate of cells, especially of fibroblasts and of myofibroblasts, covered by injured and hyperplastic epithelium, and ECM produced by myofibroblasts [Kuhn C, McDonald J A., Am J Pathol. 1991; 138:1257-1265]. Studies have revealed that IPF patients with a high number of fibroblast foci have a shortened survival [Kaarteenaho R., Respir Res. 2013; 14(1): 43]. In addition, the extent of expression of alpha smooth muscle actin (α-SMA), as a marker of myofibroblasts, in the lungs of IPF-patients, has been shown to be negatively associated with patient survival [Waisberg D R, Parra E R, Barbas-Filho J V, Fernezlian S, Capelozzi V L]. Increased fibroblast telomerase expression precedes myofibroblast alpha-smooth muscle actin expression in idiopathic pulmonary fibrosis [Clinics (Sao Paulo) 2012; 67:1039-1046].

Current paradigms of pathogenesis of fibrotic processes suggest that following exposure to endogenous or exogenous stimuli, the lung epithelium initiates an injury response resulting in the production of soluble factors such as Transforming Growth Factor beta-1 (TGF-β1), platelet-derived growth factor (PDGF), connective tissue growth factor (CTGF), and cytokines including interleukin-4 (IL-4) and interleukin-13 (IL-13). These substances promote recruitment of inflammatory cells and mesenchymal activation which causes expansion of tissue resident post-embryonic fibroblasts which are thought to give rise to activated myofibroblasts. These cells are central to the process of wound healing but, if unmodulated, deposit excessive ECM and destroy normal lung architecture. During normal wound healing, myofibroblasts are transiently activated and direct production of granulation tissue by producing ECM and exerting traction forces. Once healing is achieved, granulation tissue is resorbed and myofibroblasts undergo programmed cell death to restore normal tissue architecture and function [Klingberg et al, J Pathol. 2013; 229: 298-309]. Disruptions at any stage in this process could cause tissue pathology. When the healing response is insufficient, as is seen in acute respiratory distress syndrome, a pathology dominated by acute injury and diffuse alveolar damage ensues. However, when the healing phase dominates, the tissue milieu shifts towards fibrosis and remodeling and a pathology dominated by the dysregulated accumulation of scar tissue is seen. Fibroblasts and activated myofibroblasts are believed to be central to this process [Moore et al Curr Pathobiol Rep. 2013 September; 1 (3): 199-208].

In a further level, fibroblasts and myofibroblasts in IPF demonstrate a pathologic phenotype characterized by uncontrolled proliferation and survival. These cells accumulate in lung interstitium where they deposit excessive amounts of collagen-I rich ECM and ultimately organize into the fibroblastic foci described above. As these regions expand and become juxtaposed to the alveolar space, they appear to first rupture and then ultimately destroy the alveolar basement membrane [White et al, J Pathol. 2003; 201: 343-354].

This expansion is largely attributed to the resistance to programmed cell death that has been described for primary fibroblasts obtained from IPF lung tissue [Maher et al, Am J Respir Crit Care Med. 2010; 182: 73-82 and Nho et al, PLoS one 2013; 8]. Several possible mechanisms are proposed for this observation including abnormalities in apoptotic pathways, aberrant Wnt signaling [Chang et al, J Biol Chem. 2010; 285; 8196-8206], and defective autophagy [Patel et al, PLoS One 2012; 7].

However, a number of well characterized cytokines, including TGF-β, have been either found in injured lungs or had been produced by inflammatory cells removed from the lung. Further, in an animal model of pulmonary fibrosis, TGF-β production was increased prior to collagen synthesis and was mainly produced by alveolar macrophages. In advanced idiopathic pulmonary fibrosis extensive TGF-β deposition can be detected by immunohistochemical staining, primarily in epithelial cells in areas of lung regeneration and remodelling. This suggests that the pathogenesis of the progressive fibrosis characteristic of lung diseases such as ILDs, PF-ILDs and IPF may be an aberrant repair process (see Khali et al Ciba Found Symp. 1991; 157: 194-207 and Cutroneo et al, J. Cell. Physiol. 211: 585-589, 2007.

From this background information on fibrosis it is clear that the pathology of fibrotic processes underlying ILDs, PF-ILDs and in particular IPF can be divided into "three different levels of pathogenesis of fibrotic processes", whereby the chronological order especially of the second and the third level is not yet fully understood and could also partially take place in parallel.

In a first level of fibrotic processes, following exposure to endogenous or exogenous stimuli, the lung epithelium usually initiates an injury response resulting in the production of soluble factors such as Transforming Growth Factor beta-1 (TGF-β1), cytokines and of profibrotic mediators/fibrotic markers such as for instance procollagen, fibronectin and MCP-1.

Then, in a second level of pathogenesis of fibrotic processes, these profibrotic mediators/fibrotic markers promote mesenchymal activation which causes expansion of tissue resident post-embryonic fibroblasts which are thought to give rise to myofibroblasts, an activated form of fibroblasts. These myofibroblasts are central to the process of wound healing, but if unmodulated, they produce excessive amounts of extracellular matrix material and collagen/scar tissue. This "myofibroblast phenotype" is further characterized by a strong α-smooth muscle actin (α-SMA) expression. The transformation/activation of fibroblasts into myofibroblast, which strongly express α-SMA protein, forms the second level of pathogenesis of fibrotic processes common to ILDs, PF-ILDs and IPF.

Consequently quantification of the α-smooth muscle actin (α-SMA) protein expression is a suitable measurement for the extent of transformation/activiation of fibroblasts into myofibroblasts which corresponds to the second level of pathogenesis of fibrotic processes common to ILDs, PF-ILDs and IPF.

The third level of pathogenesis of fibrotic processes common to ILDs, PF-ILDs and IPF is characterized by uncontrolled proliferation/cell division and survival of fibroblasts and myofibroblasts, probably by their resistance to programmed cell death. Proliferating fibroblasts and myofibroblasts accumulate in lung interstitium where they deposit excessive amounts of collagen-I rich ECM and ultimately organize into the fibroblastic foci.

Quantification of cell division (for instance by quantification of incorporation of BrdU into the DNA of proliferating fibroblasts) is a suitable measurement for the extent of proliferation of fibroblasts which corresponds to the third level of pathogenesis of fibrotic processes common to ILDs, PF-ILDs and IPF.

6.2 Principle of Experimental Assays A) and B):

Lung fibroblasts of IPF-patients (IPF-LF cells) grown in 96-well plates were incubated for 30 min with different concentrations of the PDE4 inhibitors "Compound of formula III", "Apremilast" or "Roflumilast-N-Oxide" or with a combination of each of the aforementioned PDE4-inhibitiors with Nintedanib.

After compound incubation cells were stimulated with the assay-relevant stimulus and incubated for the assay—relevant time in the presence of the test compounds.

α-SMA protein was determined by a Western-replacement assay (MSD) using monoclonal anti smooth muscle actin antibodies.

BrdU incorporated in the DNA of proliferating cells was determined by ELISA. BrdU is an analog of the DNA precursor thymidine. In proliferating cells, the DNA has to be replicated before the division can take place. If BrdU is added to the cell culture, proliferating cells will incorporate it into their DNA just like they would incorporate thymidine. The amount of BrdU in the DNA of cells can be detected with specific anti-BrdU fluorescent antibodies followed by flow cytometry or by cellular ELISA with monoclonal antibodies against BrdU.

6.3 Experiment A): α-SMA (Smooth Muscle Actin) Protein Assay (Western Replacement Assay)

Cell Seeding and Starvation

IPF-lung fibroblasts (passage 5 to 8) were seeded in 96-well cell culture plates at 4500 cells/well with 100 µL/well FBM+supplements. 24 h after seeding the cells were washed once with FBM medium without supplements and starved for 24 h.

Experiment A1)

In experiment A1) the PDE4B-inhibitor of formula III was used as a "test compound"
- in rising concentrations either alone (see full circles and black solid curve in FIG. 1) or
- in rising concentrations together with a fixed concentration of 100 nMol/L of Nintedanib (see empty circles and grey solid line in FIG. 1).

Experiment A2)

In experiment A2) Apremilast was used as a "test compound"
- in rising concentrations either alone (see full circles and black solid curve in FIG. 2) or
- in rising concentrations together with a fixed concentration of 100 nMol/L of Nintedanib (see empty circles and grey solid line in FIG. 2).

Experiment A3) In experiment A3) Roflumilast-N-oxide was used as a "test compound" in rising concentrations either alone (see full circles and black solid curve in FIG. 3) or in rising concentrations together with a fixed concentration of 100 nMol/L of Nintedanib (see empty circles and grey solid line in FIG. 3).

Test Compound Dilutions

All "test compounds" (the PDE4B-inhibitor of formula III, Apremilast or Roflumilast) were prepared 1000× in 0.1 mmol/L HCl or DMSO and a 1:3.16 dilution series was performed (in 0.1 mmol/L HCl or DMSO). To obtain 2× concentrated compound-medium a 1:500 dilution (2 µl of the 1000× dilution was added to 998 µl FBM plus 2 nmol/L PGE2) was prepared.

Pre-Incubation with Test Compounds 48 h after seeding, the medium was aspirated and FBM (100 μl per well) was added. After 1 h incubation at 37° C., 90 μl medium containing 2× concentrated compounds (at different concentrations) plus 2× concentrated PGE2 (2 nmol/L) was added for 30 min. Final concentration for PGE2 was 1 nmol/L.

Stimulation 30 min after test compound pre-incubation (190 μL), 10 μl of 20× concentrated TGF-β was added and the cells stimulated for 48 h at a temperature of 37° C.

For this purpose the TGF-β stock solution (20 μg/mL reconstituted in 4 mmol/L sterile HCL) was diluted 1:200 in starvation medium to reach a concentration of 100 ng/mL. 10 μL of this TGF-β medium or starvation medium was added to indicated wells. The test compound concentration was maintained during the stimulation. The final TGF-β concentration was 4 ng/mL.

Protein Lysates 48 h after stimulation supernatants were removed and stored at −80° C. for further experiments. Cells were washed once with ice cold PBS and 50 μl RIPA buffer containing 1× protease inhibitor was added per well. Lysates were incubated for 5 minutes on ice before stored at −80° C.

α-SMA Western Replacement Assay

After thawing, 25 μl of each lysate was transferred to the membrane of the multi-array 96 well plate (MSD) and incubated for 2 h at room temperature with gentle shaking. After the incubation time, plates were washed 3 times with 200 μl 1× Tris-wash buffer (MSD) and 150 μl of 3% blocking buffer was added for 1 h. After blocking, plates were washed 3 times with 200 μl 1× Tris-wash buffer and 25 μl of the antibody solution (per plate 0.75 ml 3% blocking buffer, 2.25 ml 1× Tris-wash buffer, 1.2 μl anti-α-SMA antibody (1:2500), 15 μl goat anti-mouse sulfo-tag antibody (1:200) was added for 1 h. After AB-incubation plates were washed 3 times with 200 μl 1× Tris-wash buffer and 150 μl of 1×MSD read buffer was added per well. Plates were measured with Sector Imager (MSD).

6.4 Experiment B: Cell Proliferation Assay

Cell Seeding and Starvation

IPF-lung fibroblasts (passage 5 to 8) were seeded in 96-well cell culture plates at 2500 cells/well with 100 μL/well FBM+supplements. 24 h after seeding the cells were washed once with FBM medium without supplements and then kept in this medium for 24 h starvation.

Experiment B1)

Figure 4:
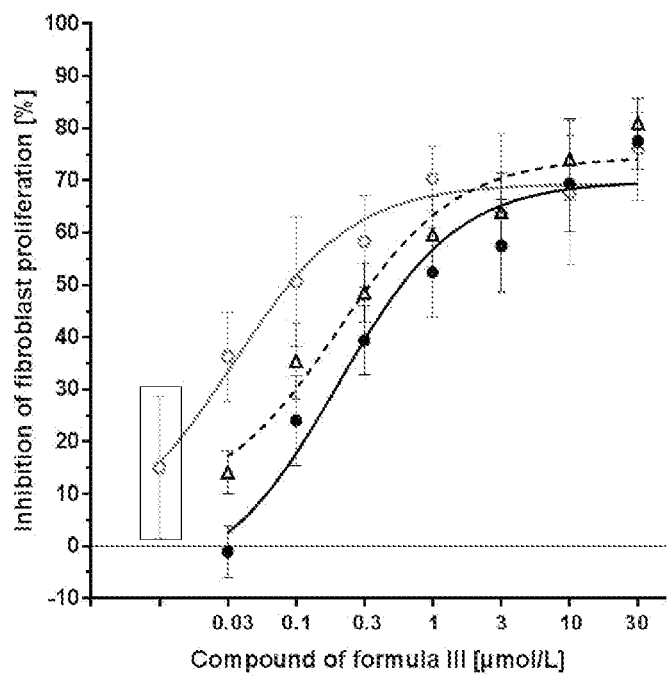

In experiment B1) the PDE4B-inhibitor of formula III was used as a "test compound"
  in rising concentrations either alone (see full circles and black solid curve in FIG. 4) or
  in rising concentrations together with a fixed concentration of 100 nMol/L of Nintedanib (see empty circles and grey solid line in FIG. 4).

The dashed line with the empty triangles represents the "calculated additive curve" of a combination treatment of 100 nMol/L Nintedanib with the corresponding concentration of the PDE4B-inhibitor of formula III.

Experiment B2)

Figure 5:
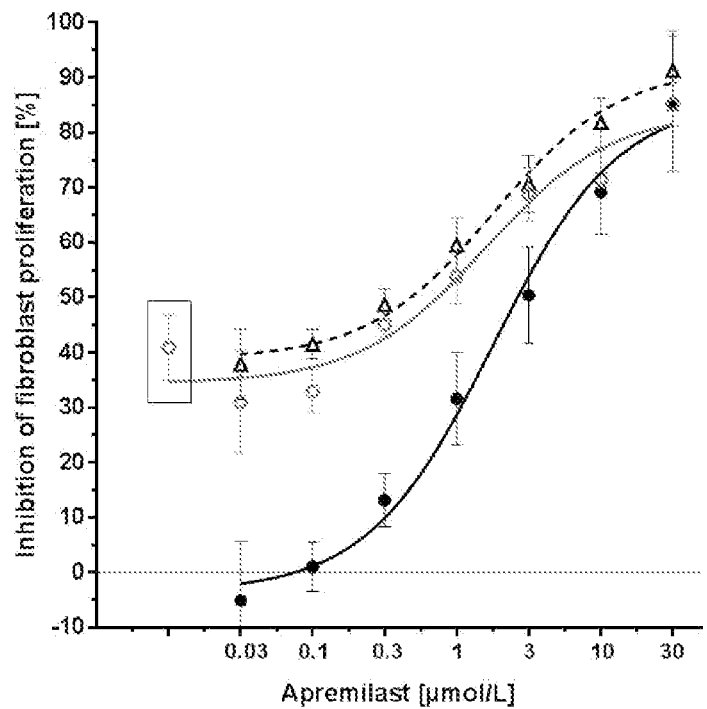

In experiment B2) Apremilast was used as a "test compound"
  in rising concentrations either alone (see full circles and black solid curve in FIG. 5) or
  in rising concentrations together with a fixed concentration of 100 nMol/L of Nintedanib (see empty circles and grey solid line in FIG. 5).

The dashed line with the empty triangles represents the "calculated additive curve" of a combination treatment of 100 nMol/L Nintedanib with the corresponding concentration of Apremilast.

Experiment B3)

Figure 6:
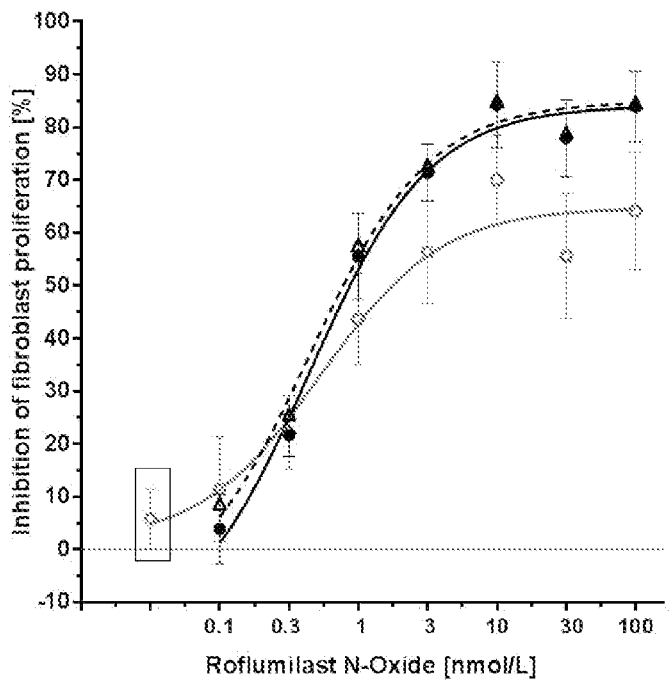

In experiment B3) Roflumilast-N-oxide was used as a "test compound"
  in rising concentrations either alone (see full circles and black solid curve in FIG. 6) or
  in rising concentrations together with a fixed concentration of 100 nMol/L of Nintedanib (see empty circles and grey solid line in FIG. 6).

The dashed line with the empty triangles represents the "calculated additive curve" of a combination treatment of 100 nMol/L Nintedanib with the corresponding concentration of Roflumilast-N-oxide.

Test Compound Dilutions

All test compounds were prepared 1000× in 0.1 mmol/L HCl or DMSO and a 1:3.16 dilution series was performed (in 0.1 mmol/L HCl or DMSO). To obtain 1× concentrated compound medium 1 μl of the 1000×DMSO dilution was added to 999 μl FBM.

Pre-Incubation with Test Compounds 48 h after seeding, medium was removed by suction and 90 μl compound- or starvation medium was added for 30 min.

Stimulation 30 min after test compound pre-incubation (90 μL), 10 μl of 10× concentrated FGF plus M-1β was added and the cells were stimulated for 92 h at a temperature of 37° C. For this purpose the FGF and IL-1β stock solutions (250 μg/mL and 10 μg/mL respectively) were diluted in starvation medium to reach a concentration of 200 ng/mL and 300 pg/mL for FGF and IL-1β respectively. 10 μL of this stimulus medium or starvation medium was added to the indicated wells. The test compound concentration was maintained during the stimulation.

The final FGF concentration was 20 ng/mL. The final IL-1β concentration was 30 pg/mL.

BrdU Assay

Proliferation was determined by a colorimetric immunoassay for the quantification of cell proliferation, based on the measurement of BrdU incorporation during DNA synthesis. The assay was carried out according to the manufacturer's instructions. 72 h after stimulation a 1:100 dilution of BrdU in starvation medium (resulting concentration 100 μmol/L) was performed and 10 μl added per well (end-concentration per well 10 μmol/l). About 18 h later the BrdU medium was removed by suction. Cells were fixed and denatured for 30 min at room temperature with FixDenat reagent. The reagent was removed by tapping and the anti-BrdU-POD working solution was added (incubation time: 90 min). The plate was washed three times with 200 μL washing buffer before incubation with substrate solution for about 10 min. The reaction was stopped by adding 1 mol/L $H_2SO_4$ to the substrate solution and plates were read at 450 nm in a photometer (EnVision 2104 Multilabel reader, PerkinElmer).

6.5 Data Analysis x-fold of unstimulated control was calculated from optical density readings (OD) for BrdU assay or from MSD units (α-SMA assay).

The % inhibition-value was calculated from the x-fold of unstimulated control. In each of the experiments for the different donors all inhibition values were determined in duplicates or triplicates.

Means of blanks were subtracted from all values.

The $IC_{50}$—values of stimulated cells were determined as follows:

% inhibition-value=100−(Y/K1)*100

K1=mean of ODs of stimulated, non-compound-treated control wells minus mean of ODs of non-stimulated, non-compound-treated control wells Y=OD of stimulated, compound-treated well Non-linear regression of log (inhibitor concentration) versus % inhibition-value was calculated using three parameter fitting with variable slope of the Graph Pad Prism Software package.

To calculate the additive effect of the compound of formula III, Apremilast or Roflumilast-N-Oxide combined with Nintedanib the following formula was used Effect of PDE4inhibitor(EB)+effect of Nintedanib (EN)=EB+N=EB+EN−(EB*EN)=dashed curve (Poch & Holzmann,1980).

TEST Compounds

The test compounds Compound of formula III, Apremilast, Roflumilast-N-Oxide, and Nintedanib were dissolved in DMSO and stored at −20° C. A serial dilution of 7 concentrations was prepared before each experiment.

6.6 Material and Methods

| Material | | |
|---|---|---|
| Test Article | Provider | Order number |
| IPF-LF cell line (passage 5 to 8) | Asterand | DI16769 |
| | | DI16783 |
| | | DI19873 |
| | | BI209755 |
| | | BI210978 |
| | | BI212020 |
| rhTGF-β | R&DSystems | 240-B-010 |
| rhFGF basic | R&DSystems | 234_FSE |
| rhIL-1β | R&DSystems | 201-LB-005 |
| rhPGE2 | Tocris | 2296 |
| Monoclonal anti smooth muscle actin antibody | Sigma | A2547 |
| Goat anti-mouse sulfo-tag antibody | MSD | R32AC-1 |
| Multi-Array 96-well Plate High Bind plates | MSD | L15XB-3 |
| MSD Blocker A | MSD | R93BA-4 |
| MSD Tris Wash Buffer (10x) | MSD | R61TX-1 |
| MSD Read Buffer T (4x) | MSD | R92TC-2 |
| RIPA buffer | Sigma | R0278-500ML |
| Halt Protease-Inhibitor cocktail (100x) | ThermoScientific | 78437 |
| PBS | Gibco | 10010023 |
| BrdU-Assay | Roche | 11647229001 |
| Cell culture flask, 75 cm², tissue-culture treated | BD Falcon™ | 353110 |
| Cell culture flask, 175 cm², tissue-culture treated | BD Falcon™ | 353112 |
| 96-well plate (cell culture) | Nunc microwell 96F | 167008 |
| DMSO | Merck | 1.02952.1000 |
| Cells-to-CT 1 Step TaqMan kit | Ambion | A25602 |

Cell Propagation Media:

FBM (fibroblast basal medium, Lonza, Cat. No: CC-3131) supplemented with insulin, FGF-2, 0.5% FBS, GA-1000 (all in FGM-2 SingleQuots, Lonza, Cat. No. CC-4126)

Reagents for Subculturing IPF-LF Cells:

Hepes buffered saline solution (Lonza, Cat. No. CC-5022) Trypsin/EDTA (0.25 mg/mL) (Lonza, CC-5012) TNS (trypsin neutralizing solution, Lonza, CC-5002)

Starvation Medium:
FBM without supplements

Stimulation Medium α-SMA Assay:
FBM plus 4 ng/mL rhTGF-β and 1 nmol/L PGE2

Stimulation Medium BrdU Assay:
FBM plus 20 ng/mL rhbFGF plus 30 pg/mL rhIL-1β

6.7 Interpretation of Experiments

Experiment A): Inhibition of TGF-β-stimulated α-SMA protein expression of human lung fibroblasts from patients with IPF The more a specific active agent tends to inhibit the TGF-β-stimulated α-SMA protein expression of human lung fibroblasts of IPF patients, the more this active agent will have a therapeutic effect in the second level of pathogenesis of fibrotic processes which is the transition of fibroblasts into myofibroblasts.

Consequently in this Experiment A) mimicking the second level of fibrotic processes the effect of
a) Nintedanib alone, the compound of formula III alone, Apremilast alone and Roflumilast-N-oxide alone and
b) of the compound of formula III with Nintedanib, of Apremilast with Nintedanib and of Roflumilast-N-oxide with Nintedanib on the TGF-β-stimulated α-SMA protein expression of human lung fibroblasts of IPF patients was experimentally determined.

Whereas Nintedanib-administered alone-in the concentration 100 nMol/L showed in this experiment no inhibitory effect on TGF-β-stimulated α-SMA protein expression of human lung fibroblasts (supporting the fact that Nintedanib in this concentration alone shows no therapeutic effect on the second level of pathogenesis of fibrotic processes (see □ in FIGS. 1, 2 and 3: Inhibition was ≤0), all tested PDE4-inhibitors (the compound of formula III, Apremilast and Roflumilast-N-oxide)—when administered alone and also when administered together with Nintedanib in the fixed concentration of 100 nMol/L-showed—at least in certain concentrations—a concentration-dependent inhibition on TGF-β-stimulated α-SMA protein expression of human lung fibroblasts which supports a certain therapeutic effect of all these PDE4-inhibitors in the second level of pathogenesis of fibrotic processes (the activation to myofibroblasts).

From these results it can be concluded that PDE4-inhibitors—at least in certain concentration ranges—have the potential to show a concentration-depending therapeutic effect on the "fibroblast to myofibroblast transition/activation", an event that represents the second level of pathogenesis of fibrotic processes which are common to ILDs, particularly to PF-ILDs, whereas Nintedanib in the concentration 100 nMol/L alone does not show a therapeutic effect on this very same "second level of pathogenesis" according to this experiment.

Consequently PDE4-inhibitors show in relation to Nintedanib a so-called "complementary effect" or "supplementary effect" on the "fibroblast to myofibroblast transition/activation" (=second level of pathogenesis of fibrotic processes). Therefore an administration of Nintedanib together with a PDE4B-inhibitor of formula III will show a superior effect on therapeutic efficacy compared to the IPF-treatment with for instance Nintedanib alone.

If you compare the measured inhibition on the TGF-β-stimulated α-SMA protein expression of human lung fibroblasts for the compound of formula III (FIG. 1), for Apremilast (FIG. 2) and for Roflumilast-N-oxide (FIG. 3), it is obvious that only for the compound of formula III (FIG. 1) the complete concentration/inhibition curve is located at inhibitions of "above zero", whereas for instance for Apremilast and in particular for Roflumilast-N-oxide" low PDE4-inhibitor concentrations (either alone or in combination with Nintedanib)" lead to "negative inhibitions of TGF-β-stimulated α-SMA protein expression" (supporting the absence of a therapeutic effect on the second level of fibrotic processes for Apremilast and in particular for Roflumilast-N-oxide at these lower concentrations (whereas the compound of formula III seems to show a positive inhibition of TGF-β-stimulated α-SMA protein expression in all tested concentrations).

Experiment B): Inhibition of fibroblast proliferation

The more a specific active agent tends to inhibit proliferation of cultured human lung fibroblasts of IPF patients, the more this active agent will have a therapeutic effect in the third level of pathogenesis of fibrotic processes which is fibroblast proliferation.

Consequently the effect of
a) Nintedanib alone, the compound of formula III alone, Apremilast alone and Roflumilast-N-oxide alone and
b) of the compound of formula III with Nintedanib, of Apremilast with Nintedanib and of Roflumilast-N-oxide with Nintedanib on the proliferation of human lung fibroblasts of IPF patients was experimentally determined in Experiment B).

In this experiment B) mimicking the third level of pathogenesis of fibrotic processes (the "fibroblast proliferation"), Nintedanib administered alone in the concentration 100 nMol/L already showed a clear inhibitory effect on human lung fibroblasts proliferation (see inhibition data points symbolized by □ in FIGS. 4, 5 and 6).

However, the results of Experiments B1) in FIG. 4, B2) in FIG. 5 and B3) in FIG. 6 show that not only Nintedanib alone has an inhibitory effect on fibroblast proliferation, but that also PDE4-inhibitors such as the compound of formula III (see filled circles and black solid curve in B1, FIG. 4)), Apremilast (see filled circles and black solid curve in B2, FIG. 5)) and Roflumilast-N-oxide (see filled circles and black solid curve in B3 in FIG. 6)) show in general a concentration-dependent inhibitory effect on fibroblast proliferation and therefore seem to have a therapeutic effect on fibroblast proliferation (third level of pathogenesis of fibrotic processes).

Since obviously both Nintedanib in the fixed concentration of 100 nMol/L and the tested PDE4-inhibitors concentration-dependently show an inhibitory effect on fibroblast proliferation, a simple "additive effect" for the inhibition of fibroblast proliferation by the combination of 100 nMol/L Nintedanib and the corresponding PDE4-inhibitor in its respective concentration should be expected.

In FIGS. 4, 5 and 6 the dashed curves with the empty triangles represent these "calculated additive combination curves" which were calculated from the simple "addition" of the measured inhibition-value for 100 nMol/L Nintedanib plus the measured inhibition—value for the corresponding PDE4-inhibitor alone in variable concentrations.

However, the grey solid curves with the empty circles in FIGS. 4, 5 and 6 represent the "experimentally measured inhibition-curves for the combinations comprising 100 nMol/L Nintedanib and the corresponding PDE4-inhibitor in variable concentrations".

Surprisingly, in FIG. 4 which shows the results of Experiment B1) the "experimentally measured inhibition curve of fibroblast proliferation" for the combination of Nintedanib with the compound of formula III (solid grey line, empty circles) is "significantly shifted to the left" (that means towards lower concentrations of the compound of formula III) compared to the corresponding "calculated additive inhibition curve" for the combination of Nintedanib with the compound of formula III (dashed curve with empty triangles).

This significant "left-shift" is a clear indicator for an "overadditive synergistic effect" of the combination of 100 nMol/L Nintedanib with the compound of formula III. This experimentally observed "overadditive synergistic effect" for the combination of Nintedanib and the compound of formula III was completely surprising, in particular because this synergistic overadditive effect does not seem to be a "class effect".

FIG. 5 shows the results of the corresponding Experiment B2), wherein the compound of formula III was exchanged by Apremilast. FIG. 5 shows that the "experimentally measured inhibition curve" for the combination of Nintedanib with Apremilast (solid grey line, empty circles) is not shifted to the left, but instead is even slightly shifted to the right (that means to higher Apremilast concentrations) compared to the corresponding "calculated additive inhibition curve" for the combination of Nintedanib with Apremilast (dashed curve with empty triangles). Such a "right-shift" would theoretically even be an indicator for a "less than additive inhibition of fibroblast proliferation" (an "anti-synergistic effect") by the combination of Nintedanib and Apremilast. However, this rather slight right-shift of the "measured Nintedanib/Apremilast combination curve" compared to the "calculated Nintedanib/Apremilast combination curve" is more or less within the error bars and therefore not statistically relevant. Consequently, for the combination of Nintedanib with Apremilast more or less a normal "addititve effect" as expected could be experimentally observed.

FIG. 6 shows the results of the corresponding Experiment B3), wherein the compound of formula III was exchanged by Roflumilast-N-oxide. FIG. 6 shows that the "experimentally measured inhibition curve" for the combination of Nintedanib with Roflumilast-N-oxide (solid grey line, empty circles) is also shifted to the right instead to the left compared to the corresponding "calculated additive inhibition curve" for the combination of Nintedanib with Roflumilast-N-oxide (dashed curve with empty triangles). Such a "right-shift" is an indicator for a "less than additive inhibition of fibroblast proliferation" (anti-synergistic effect) for the combination of Nintedanib and Roflumilast-N-oxide. This "right-shift" of the "measured Nintedanib/Roflumilast combination curve" compared to the "calculated Nintedanib/ Roflumilast combination curve" is only for very high Roflumilast-N-oxide concentration beyond the error bar ranges. Consequently for the combination of Nintedanib with Roflumilast-N-oxide also a more or less "additive effect" as expected could be experimentally determined.

This "overadditive synergistic effect" on the inhibition of fibroblast proliferation which was exclusively observed for the combination of Nintedanib with the compound of formula III is also reflected in the large differences of the $IC_{50}$-values calculated for the concentration/inhibition curves
a) measured for human lung fibroblast of IPF patients treated with the compound of formula III alone in FIG. 4 (solid black curve, $IC_{50}$-value of 255 nMol/L) and
b) measured for human lung fibroblast of IPF patients treated with the combination comprising the compound of formula III and Nintedanib in FIG. 4 (solid grey curve, $IC_{50}$-value of 23 nMol/L).

Here the $IC_{50}$-value for the inhibition curve measured for the compound of formula III administered alone is compared to the $IC_{50}$-value for the inhibition curve measured for the combination of the compound of formula III with Nintedanib 11-fold larger (255 nMol/L/23 nMol/L=11).

In contrast to that, the corresponding differences in the $IC_{50}$-values for the inhibition curves measured for the other PDE4-inhibitors Apremilast and Roflumilast-N-oxide administered alone compared to the inhibition curve measured for the corresponding PDE4-inhibitor/Nintedanib combinations were much smaller (1,13-fold larger for Apremilast, 0.82-fold smaller for Roflumilast-N-oxide).

This experimentally determined "overadditive synergistic effect" on the inhibition of fibroblast proliferation which was exclusively observed for the combination of the compound of formula III with Nintedanib obviously does not seem to be a "class effect", since none of the other tested PDE4-inhibitors Apremilast or Roflumilast showed in combination with Nintedanib a corresponding similar "overadditive synergistic effect", but instead only the expected "additive inhibitory effect" (Nintedanib/Roflumilast-N-oxide showed at large Roflumilast-N-oxide-concentrations even a "less than additive inhibitory effect").

Consequently the combination of Nintedanib with the PDE4B-inhibitor of formula III shows due to the experimentally observed overadditive synergistic inhibitory effect on fibroblast proliferation surprisingly a clearly improved therapeutic efficacy for the treatment of PF-ILD-patients not only compared to treatment with the individual single agents, but also compared to the alternative combinations Nintedanib/Roflumilast-N-oxide and Nintedanib/Apremilast.

Consequently Experiments A) and B) have experimentally shown that the combination comprising the PDE4B-inhibitor of formula III and Nintedanib shows 1.) on the "second level of pathogenesis of fibrotic processes common to PF-ILDs" (activation of fibroblasts to myofibroblasts) a clear therapeutic effect over the complete range of tested concentrations for the PDE4B-inhibitor of formula III (whereby Nintedanib alone showed no therapeutic effect on the second level) and 2.) on the "third level of pathogenesis of fibrotic processes common to PF-ILDs" (fibroblast proliferation) surprisingly even an "overadditive synergistic therapeutic effect" (which the Roflumilast-N-oxide/Nintedanib- and Apremilast/Nintedanib-combinations surprisingly did not show).

Another additional advantage the combination of the PDE4B-inhibitor of formula III with Nintedanib obviously shows compared to other PDE4-inhibitor/Nintedanib combinations (such as for instance Roflumilast-N-oxide/Nintedanib) is its relatively good tolerability (in particularly with respect to gastrointestinal side effects).

It is known that Nintedanib and also Pirfenidone—the presently two only approved therapeutic agents for the treatment of IPF—show both significant gastrointestinal side effects such as diarrhea, nausea, vomiting, weight loss etc. which is the main reason why Nintedanib and Pirfenidone are usually not combined due to their additive and therefore more frequent gastrointestinal side effects.

In contrast to Nintedanib and Pirfenidone, the PDE4B-inhibitor of formula III has been shown to be relatively free of the PDE4-inhibitor-typical gastrointestinal side effects such as diarrhea in a corresponding rat experiment (see WO 2013/026797 Chapter 5.3: Experiments of "gastric emptying" and "intestinal transit" and FIG. 2a (gastric emptying) and 2b (intestinal transit)). In these experiments it could be shown that a rising amount of Example compound No. 2 (which is identical to the PDE4B-inhibitor of formula III in the present application) had basically no effect on the gastric emptying and on the intestinal transit of a test meal in the rat compared to non-treated rats.

However, in similar "gastric emptying" and "intestinal transit" experiments the alternative PDE4-inhibitor Roflumilast has shown a clear trend to show gastrointestinal side effects.

Additionally, it is also well known from clinical trials that Roflumilast (which is only authorized for the treatment of COPD) shows significant gastrointestinal side effects in human COPD-patients such as diarrhea, nausea, weight loss.

In http://www.rxlist.com/daliresp-drug.htm it is disclosed that Roflumilast given to COPD-patients in a dose of 500 µg daily lead in 9.5% of all patients to diarrhea (compared to only 2.7% to the patients receiving placebo)

in 4.7% of all patients to nausea (compared to only 1.4% to the patients receiving placebo)

in 7.5% of all patients to decreased weight (compared to only 2.1% to the patients receiving placebo) and in 4.4% of all patients to headache (compared to only 2.1% to the patients receiving placebo).

Due to the observations mentioned above the combination of the PDE4B-inhibitor of formula III with Nintedanib has a better tolerability with respect to gastrointestinal side effects compared to for example a combination of Roflumilast with Nintedanib. Additionally the combination of the PDE4B-inhibitor of formula III with Nintedanib has a better therapeutic efficacy with respect to treating ILDs, PF-ILDs and in particular IPF (see FIG. 1-6) combined with an acceptable tolerance with respect to gastrointestinal side effects (WO 2013/026797 Chapter 5.3).

The invention claimed is:

1. A pharmaceutical composition comprising:

a PDE4B-inhibitor of formula III

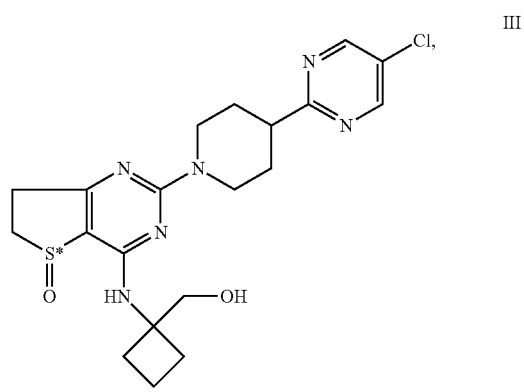

wherein S* is a sulphur atom that represents a chiral center,

Nintedanib in the form of its monoethanesulfonate, and optionally, one or more pharmaceutically acceptable carriers and/or excipients.

2. A kit comprising:

a first pharmaceutical composition or dosage form comprising a PDE4B-inhibitor of formula III

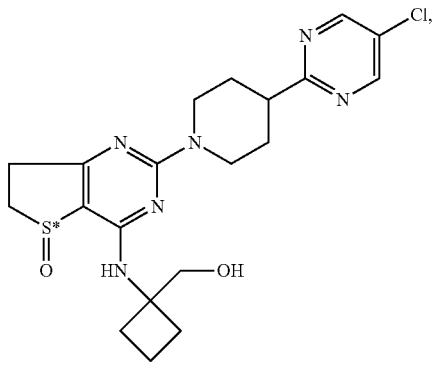

wherein S* is a sulphur atom that represents a chiral center, and optionally, one or more pharmaceutically acceptable carriers and/or excipients; and a second pharmaceutical composition or dosage form comprising Nintedanib in the form of its monoethanesulfonate and, optionally, one or more pharmaceutically acceptable carriers and/or excipients.

3. The kit according to claim 2, further comprising a package insert comprising printed instructions for simultaneous, concurrent, sequential, successive, alternate or separate use of the first and the second pharmaceutical composition or dosage forms in the treatment of one or more Progressive Fibrosing Interstitial Lung Diseases (PF-ILDs).

4. The kit according to claim 2, further comprising a package insert comprising printed instructions for simultaneous, concurrent, sequential, successive, alternate or separate use of the first and the second pharmaceutical composition or dosage forms in the treatment of Idiopathic Pulmonary Fibrosis (IPF).

5. A method of treating one or more Progressive Fibrosing Interstitial Lung Diseases (PF-ILDs), comprising administering to a patient in need thereof a therapeutically effective amount of a PDE4B-inhibitor of formula III

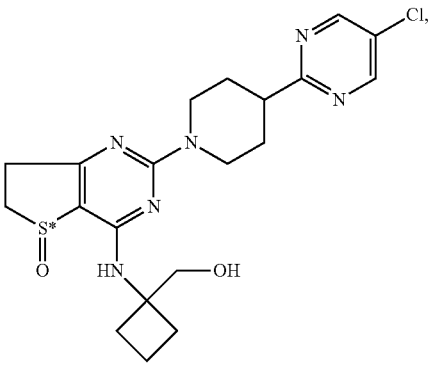

wherein S* is a sulphur atom that represents a chiral center, and a therapeutically effective amount of Nintedanib in the form of its monoethanesulfonate.

6. The method of claim 5, wherein the Progessive Fibrosing Interstitial Lung Disease is Idiopathic Pulmonary Fibrosis (IPF).

7. The method according to claim 5, wherein the PDE4B-inhibitor of formula III is administered simultaneously, concurrently, sequentially, successively, alternately or separately with the Nintedanib in the form of its monoethanesulfonate.

* * * * *